(12) United States Patent
Yu et al.

(10) Patent No.: US 10,378,058 B2
(45) Date of Patent: *Aug. 13, 2019

(54) DIAGNOSTIC AND THERAPEUTIC METHODS AND COMPOSITIONS INVOLVING PTEN AND BREAST CANCER

(75) Inventors: Dihua Yu, Houston, TX (US); Xiaoyan Zhou, Shanghai (CN); Yoichi Nagata, Tosu (JP); Francisco J. Esteva, Bellaire, TX (US); Aysegul A. Sahin, Houston, TX (US)

(73) Assignee: Board of Regents of The University of Texas System, Austin, TX (US)

( * ) Notice: Subject to any disclaimer, the term of this patent is extended or adjusted under 35 U.S.C. 154(b) by 1835 days.

This patent is subject to a terminal disclaimer.

(21) Appl. No.: 12/943,644

(22) Filed: Nov. 10, 2010

(65) Prior Publication Data

US 2011/0150868 A1    Jun. 23, 2011

Related U.S. Application Data

(63) Continuation of application No. 10/983,011, filed on Nov. 5, 2004, now Pat. No. 7,981,618.

(60) Provisional application No. 60/517,559, filed on Nov. 5, 2003.

(51) Int. Cl.

| | |
|---|---|
| C12Q 1/6886 | (2018.01) |
| C12Q 1/42 | (2006.01) |
| G01N 33/50 | (2006.01) |
| G01N 33/573 | (2006.01) |
| G01N 33/574 | (2006.01) |

(52) U.S. Cl.
CPC .......... *C12Q 1/6886* (2013.01); *C12Q 1/42* (2013.01); *G01N 33/5011* (2013.01); *G01N 33/573* (2013.01); *G01N 33/57415* (2013.01); *C12Q 2600/106* (2013.01); *Y10T 436/25* (2015.01)

(58) Field of Classification Search
CPC ...... C12Q 1/00; C12Q 3/00; C12Q 2600/106; C12Q 2600/158; A61K 6/00; A61K 49/00; A61K 49/0004
See application file for complete search history.

(56) References Cited

U.S. PATENT DOCUMENTS

| | | | |
|---|---|---|---|
| 6,020,199 A | 2/2000 | Monia et al. | |
| 6,262,242 B1 | 7/2001 | Steck et al. | |
| 7,981,618 B2 * | 7/2011 | Yu et al. | 435/7.1 |
| 2002/0150954 A1 | 10/2002 | Durden | |
| 2003/0059464 A1 | 3/2003 | Ravkin et al. | |
| 2003/0059764 A1 | 3/2003 | Ravkin et al. | |

FOREIGN PATENT DOCUMENTS

| | | |
|---|---|---|
| WO | WO 2006/044748 | 4/2006 |
| WO | WO 2005/044091 A2 | 5/2008 |

OTHER PUBLICATIONS

Stark et al. PI3K inhibitors in inflammation, autoimmunity and cancer. (Current Opinion in Pharmacology 82-91, 2015).*
McMenamin et al. Loss of PTEN expression in paraffin-embedded primary prostate cancer correlates with high gleason score and advanced stage. (Cancer Research 59: 4291-4296, Sep. 1, 1999).*
Hu et al. Inhibition of phosphatidylinositol 3'-kinase increases efficacy of paclitaxel in in vitro and in vivo ovarian cancer models. (Cancer Research 62: 087-1092, Feb. 15, 2002).*
Massacesi et al. PI3K inhibitors as new cancer therapeutics: implications for clinical trial design. OncoTargets and Therapy 9: 203-210, 2016.*
Naguib et al., "Alterations in PTEN and PIK2CA in colorectal cancers in the EPIC Norfolk study: associations with clinicopathological and dietary factors", BMC Cancer, 2011, 11:123, 11 pages.
Albanell et al., "Unraveling resistance to trastuzumab (Herceptin): insulin-like growth factor-1 receptor, a new suspect," *J. Nat/. Cancer Inst.*, 93(24): 1830-1832, 2001.
Bacus et al.,"Differences in response of breast cancer molecular profiles of patients likely to respond either to erbB tyrosine kinase inhibitors or to erbB targeted antibodies", Nov. 24, 2003, *Abstract 314*, 82(Suppl. 1): S72-73.
Bael, "Predictive value of HER-2/Neu over-expression and PTEN deletion in high-risk primary breast cancer patients treated with high-dose chemotherapy and stem-cell support", *2nd Year Research Elective Resident's Journal*, V: 8-13, 2000-2001.
Bange et al., "Molecular targets for breast cancer therapy and prevention," *Nat. Med.*, 2001, 7(5):548-552.
Baselga et al., "Phase II study of weekly intravenous recombinant humanized anti-p185HER2 monoclonal antibody in patients with HER2/neu-overexpressing metastatic breast cancer," *J. Clin., Oncol.*, 14(3):737-744, 1996.
Belsches-Jablonski et al., "Src family kinases and HER2 interactions in human breast cancer cell growth and survival," *Oncogene*, 20:1465-1475, 2001.
Cantley et al., "New insights into tumor suppression: PTEN suppresses tumor formation by restraining the phosphoinositi~e 3-kinase/ AKT pathway," *Proc. Nat!. Acad. Sci. USA*, 96(8):4240-4245, 1999.
Cobleigh et al., "Multinational study of the efficacy and safety of humanized anti-HER2 monoclonal antibody in women who have HER2-overexpressing metastatic breast cancer that has progressed after chemotherapy for metastatic disease," *J. Clin., Oncol.*, 17(9):2639-2648, 1999.
Comer et al., "PI 3-kinases and PTEN: how opposites chemoattract," *Cell*, 109(5):541544, 2002.

(Continued)

*Primary Examiner* — Alana Harris Dent
(74) *Attorney, Agent, or Firm* — Fisherbroyles, LLP; Victoria L. Boyd; Frank W. Leak

(57) ABSTRACT

Patients with ErbB2-overexpressing cancers can be given an ErbB2 targeting agent as a therapeutic regimen but not all patients are responsive. The present invention concerns the diagnostic, prognostic and therapeutic methods and compositions for evaluating potential efficacy of an ErbB2 targeting agent in an ErbB2-overexpressing cancers by evaluating PTEN expression, which is predictive of responsiveness or resistance to ErbB2 targeting agents such as trastuzumab. Low PTEN expression is predictive of a patient who will respond poorly to trastuzumab.

6 Claims, 15 Drawing Sheets

Specification includes a Sequence Listing.

(56) References Cited

OTHER PUBLICATIONS

Crowder et al., *Cancer Cell*, Aug. 2004, 6:103 and 104.
Depowski et al., "Loss of Expression of the PTEN gene protein product is associated with poor outcome in breast cancer", *Mod. Pathol.*, 2001, 14(7):672-676.
Di Cristofano et al., "The multiple roles ofPTEN in tumor suppression," *Cell*, 100(4):387-390, 2000.
Drebin et al., "Down-modulation of an oncogene protein product and reversion of the transformed phenotype by monoclonal antibodies," *Cell*, 4 I(3):697-706, 1985.
Eng, "PTEN: One Gene, Many Syndromes", *Human Mutation*, Sep. 2003, 22:183-198.
GenBank Accession No. AAC51 183, Apr. 1, 1997.
GenBank Accession No. U9305I, Apr. 1, 1997.
Georgescu et al., "The tumor-suppressor activity of PTEN is regulated by its carboxyl-terminal region," *Proc. Nat!. Acad. Sci. USA*, 96(18):10182-10187, 1999.
Hudziak et al., "p I 85HER2 monoclonal antibody has antiproliferative effects in vitro and sensitizes human breast tumor cells to tumor necrosis factor," *Mol. Cell Bioi.*, 9(3): 1165-1 172, 1989.
Ignatoski et al., "ERBB-2 overexpression confers PI 3' kinase-dependent invasion capacity on human mammary epithelial cells," *Br. J. Cancer*, 82(3):666-674,2000.
Iijima et al., "Tumor suppressor PTEN mediates sensing of chemoattractant gradients," *Cell*, 109(5):599-610, 2002.
Jacobs et al., "Comparison of fluorescence in situ hybridization and immunohistochemistry for the evaluation ofHER-2/neu in breast cancer," 1. *Clin. Oneal.*, 17(7): 1974-I982, 1999.
Joki et al., "Expression ofcyclooxygenase 2 (COX-2) in human glioma and in vitro inhibition by a specific COX-2 inhibitor, NS-398," *Cancer Res.*, 60(17):4926-31,2000.
Koul et al., "Motifanalysis of the tumor suppressor gene MMACIPTEN identifies tyrosines critical for tumor suppression and lipid phosphatase activity," *Oncogene*, 2 1:2357-2364, 2002.
Lee et al., "Expression ofsmall interfering RNAs targeted against mv-1 rev transcripts in human cells," *Nature Biotechnology*, 19:500-505, 2002.
Leslie et al., "PTEN: The down side of PI 3-kinase signaling," *Cell Signal*, 14(4):285295,2002.
Li et al., "PTENIMMACI/TEPI suppresses the tumorigenicity and induces GI cell cycle arrest in human glioblastoma cells," *Proc. Natl.Acad. Sci.* USA, 95: 15406-15411, 1998.
Li et al., "PTEN, a putative protein tyrosine phosphatase gene mutated in human brain, breast, and prostate cancer," *Science*, 275:1943-1947, 1997.
Lu et al., "Src family protein-tyrosine kinases alter the function of PTEN to regulate phosphatidylinositol3-kinase/ AKT cascades," 1. *Bioi. Chern.*, 278:40057-40066, 2003.
Meric-Bernstam et al., "Advances in Targeting Human Epidermal Growth Factor Receptor-2 Signaling for Cancer Therapy", *Clin. Cancer Res.*, 12(21):6326-6330, 2006.
Molina et al., "Trastuzumab (herceptin), a humanized anti-Her2 receptor monoclonal antibody, inhibits basal and activated Her2 ectodomain cleavage in breast cancer cells," *Cancer Res.*, 61(12):4744-4749,2001.
Mutter et al., "Altered PTEN expression as a diagnostic marker for the earliest endometrial precancers," 1. *Natl. Cancer Inst.*, 92{I1):924-930, 2000.
Nagata et al., "PTEN activation contributes to tumor inhibition by trastuzumab, and loss of PTEN predictes trastuzumab resistance in patients," *Cancer Cell*, 6:117-127,2004.
Normanno et al., "Target-based agents against ErbB receptors and their ligands: a novel approach to cancer treatment". Endocrine-Related Cancer, 2003, 10:1-21.
Oesterreich et al., "Tumor suppressor genes in breast cancer", Endocrine-Related Cancer, 1999, 6:405-419.
Palka et al., "Roles ofplakogiobin end domains in desmosome assembly," 1. *Ceil Sci.*, IIO(pt 19):2359-71, 1997.

Pegram et al., "Phase II study ofreceptor-enhanced chemosensitivity using recombinant humanized anti-pl85HERI/neu monoclonal antibody plus cisplatin in patients with HERI/neu-overexpressing metastatic breast cancer refractory to chemotherapy treatment," 1. *CUn., Oneal.*, 16(8):2659-2671, 1998.
Perren et al., "Immunohistochemical evidence of loss of PTEN expression in primary ductal adenocarcinomas of the breast," *Am. J. Pathol.*, 155(4):1253-1260, 1999.
Petit et al., "Neutralizing antibodies against epidermal growth factor and ErbB-2/neu receptor tyrosine kinases down-regulate vascular endothelial growth factor production by tumor cells in vitro and in vivo: angiogenic implications for signal transduction therapy of solid tumors," *Am. J. Pathol.*, 151(6):1523-1530,1997.
Sano et al., "Immuno-PCR: very sensitive antigen detection by means of specific antibody-DNA conjugates," *Science*, 258(5079): 120-2, 1992.
Shepard et al., "Monoclonal antibody therapy of human cancer: taking the HERI protooncogene to the clinic," *J. Clin. Immunol.*, 11:117-127, 1991.
Slamon et al., "Use ofchemotherapy plus a monoclonal antibody against HER2 for metastatic breast cancer that overexpresses HER2," *N. Engl. J. Med.*, 344(11 ):783-792, 200I.
Sliwkowski et al., "Nonclinical studies addressing the mechanism ofaction of trastuzumab (Herceptin)," *Semin, Oneal.*, 26(4 Suppl12):60-70, 1999.
Teng et al., "MMACI/PTEN mutations in primary tumor specimens and tumor cell lines," *Cancer Res.*, 57(23):5221-5225, 1997.
Valero et al., "Phase II trial ofdocetaxel: a new, highly effective antineoplastic agent in the management of patients with anthracycline-resistant metastatic breast cancer," 1. *Clin. Oneal.*, 13:2886-2894, 1995.
Van Leeuwen et al., "Mutation of the human neu protein facilitates down-modulation by monoclonal antibodies," *Oncogene*, 5(4):497-503, 1990.
Vivanco et al., "The phosphatidylinositol 3-Kinase AKT pathway in human cancer," *Nat. Rev. Cancer*, 2(7):489-501, 2002.
Vogel et al., "Efficacy and safety oftrastuzumab as a single agent in first-line treatment of HER2-overexpressing metastatic breast cancer," *J. Clin. Oneal.*, 20(3):719-726,2002.
Whang et al., "Identification ofa pseudogene that can masquerade as a mutant allele ofthe PTEN/MMAC1 tumor suppressor gene," *J. Natl. Cancer Inst.*, 90(11):859-861, 1998.
Wu et al., "Transcriptional activation ofp2 IWAFI by PTENIM-MACI tumor suppressor," *Mol. Cell Biochem.*, 203(1-2):59-71, 2000.
Xia et al., "Lapatinib Antitumor Activity is no dependent upon Phosphatase and Tensin Homologue Deleted on Chromosome 10 in ErbB2-Overexpression Breast Cancers", Cancer Research, Feb. 1, 2007, 67(3):1170-1175.
Yakes et al., "Herceptin-induced inhibition ofphosphatidylinositol-3 kinase and Akt Is required for antibody-mediated effects on p27, cyelin DI, and antitu'mor action," *Cancer Res.*, 62(14):4132-4141,2002.
Zhou et a/., "HER-2/neu blocks tumor necrosis factor-induced apoptosis via the Akt/NFkappaB pathway," *J Bioi Chem* 275:8027-8031, 2000.
Clark et al., "Constitutive and inducible Akt activity promotes resistance to chemotherapy, trastuzumab, or tamoxifen in breast cancer cells", *Molecular Cancer Therapeutics*, 2002, 1:707-717.
Mercapide et al., "CCND1- and ERBB2-Gene deregulation and PTEN mutation analyses in invasive lobular carcinoma of the breast", *Molecular Carcinogenesis*, 2002, 35:6-12.
PCT International Search Report and Written Opinion, issued in International Application No. PCT/US2004/037023, dated Nov. 3, 2005.
PCT International Search Report and Written Opinion, issued in International Application No. PCT/US2004/037023, dated Feb. 10, 2007.
DeGraffenried et al., "Reduced PTEN expression in breast cancer cells confers susceptibility to inhibitors of the PI3 kinase/Akt pathway" Annals of Oncology, 2004, 15(10): 1510-1516.

* cited by examiner

PTEN IRS = 12

PTEN IRS = 9

PTEN IRS = 3

PTEN IRS = 0

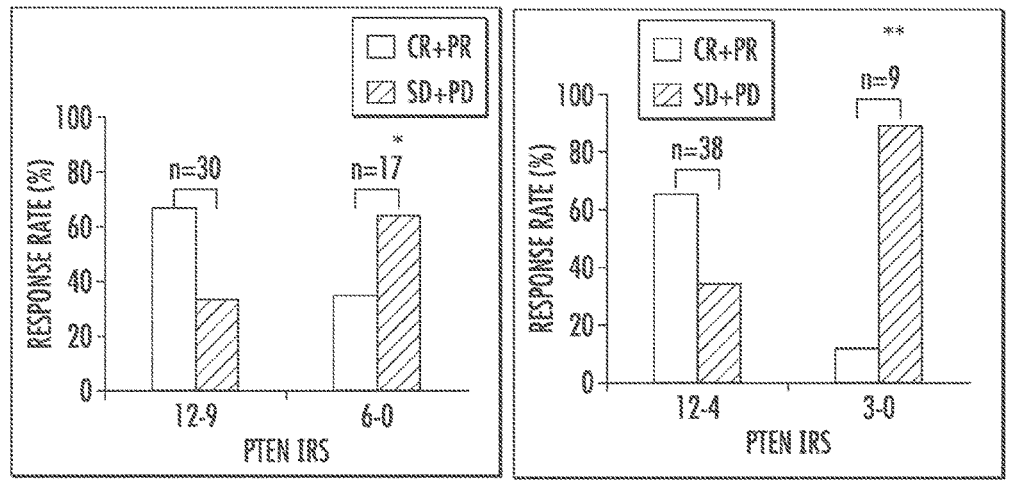
FIG. 6B
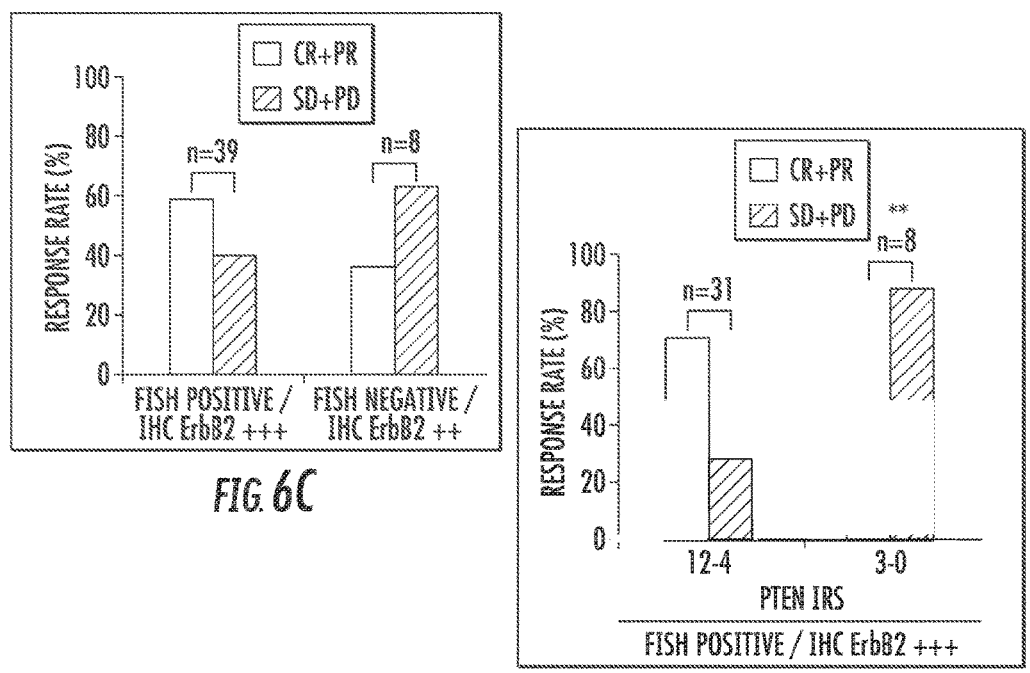
FIG. 6C
FIG. 6D

DIAGNOSTIC AND THERAPEUTIC METHODS AND COMPOSITIONS INVOLVING PTEN AND BREAST CANCER

The present application is a continuation application of U.S. Utility application Ser. No. 10/983,011, filed 5 Nov. 2004, which claims the benefit of U.S. Provisional Application Ser. No. 60/517,559 filed on Nov. 5, 2003. Each of these applications is incorporated herein by reference in their entirety.

The government may own rights in the present invention pursuant to funding from the United States Army Medical Research and Material Command No. DAMD17-02-1-0462.

SEQUENCE LISTING

A formal Sequence Listing has been submitted electronically with this application. This Sequence Listing is identical to the sequence listing in computer readable form submitted in the related U.S. Utility Application Ser. No. 10/983,011, filed Nov. 5, 2004. Its contents are incorporated by reference herein in their entirety.

BACKGROUND OF THE INVENTION

I. Field of the Invention

The present invention relates generally to the fields of molecular biology and oncology. More particularly, it concerns diagnostic, prognostic, and therapeutic methods and compositions involving ErbB2-overexpressing cancers and potential efficacy of ErbB2 targeting agents to treat such cancers. The invention involves evaluating PTEN expression and/or activity to evaluate and/or predict efficacy or possible resistance to such agents.

II. Description of Related Art

Overexpression of ErbB2, a 185 kDa membrane receptor tyrosine kinase, is found in approximately 20-30% of human breast cancers and many other cancer types (Slamon et al., 1987; Yu and Hung, 2000). ErbB2 overexpression leads to a very aggressive cancer phenotype and poor patient survival (Yu and Hung, 2000). Numerous efforts have been directed at developing ErbB2-targeting cancer therapies (Bange et al., 2001). One successful example is the recombinant humanized anti-ErbB2 monoclonal antibody trastuzumab (Herceptin) that specifically binds to the extracellular domain of ErbB2 (Shepard et al., 1991). The currently known mechanisms underlying trastuzumab's anti-tumor activity include the down-regulation of p185$^{ErbB2}$ and the subsequent inhibition of its down-stream PI3K-Akt signaling pathway (Hudziak et al., 1989; Yakes et al., 2002), the induction of G$_1$ arrest and cyclin-dependent kinase inhibitor p27$^{kip1}$ (Sliwkowski et al., 1999), and the inhibition of ErbB2 ectodomain cleavage (Molina et al., 2001). Despite these and other reported functions resulting from ErbB2 down-regulation (Petit et al., 1997), the mechanism of trastuzumab's anti-tumor activity remains a fundamental question to be clearly addressed (Albanell and Baselga, 2001).

As the first FDA approved therapeutic antibody for metastatic breast cancer, trastuzumab has demonstrated durable responses as a single agent and striking therapeutic efficacy in combination with other chemotherapeutics (Baselga et al., 1996; Cobleigh et al., 1999; Esteva et al., 2002; Pegram et al., 1998; Seidman et al., 2001; Slamon et al., 2001; Vogel et al., 2002). However, only less than 35% of patients with ErbB2-overexpressing metastatic breast cancer respond to trastuzumab as a single agent whereas ~5% patients suffer from severe side effects (e.g., cardiac dysfunction) and 40% of patients experience other adverse effects from trastuzumab treatment (Cobleigh et al., 1999; Vogel et al., 2002). Thus, there is an urgent need to identify patients who are unlikely to respond to trastuzumab treatment to spare them the potential side effects and unnecessary cost. More importantly, trastuzumab resistance-conferring factors may serve as molecular targets for overcoming trastuzumab resistance. Unfortunately, there is very limited information on mechanisms of trastuzumab resistance of breast cancer cells. Currently, there is no clinically verified factor that can be used to predict trastuzumab resistance (Albanell and Baselga, 2001).

Consequently, there is a need for a screen to evaluate whether a patient may be resistant to trastuzumab in order to prevent unnecessary side effects and costs in breast cancer patients who might otherwise receive the treatment even though they are resistant. Methods and kits for determining whether a patient might have resistance or susceptibility to an ErbB2-overexpressing cancer have not been previously known.

SUMMARY OF THE INVENTION

The present invention is based on the observation that a deficiency in PTEN activity in cancer cells is significantly associated with the resistance of those cells to ErbB2-targeting agents that are used to treat cancer. Thus, the present invention concerns diagnostic, prognostic, and therapeutic methods and compositions for cancers that involve ErbB2 expression, and consequently, ErbB2 targeting agents. It provides information about whether a particular cancer patient is more or less likely to respond or be resistant to an ErbB2 targeting agent that is being considered as a therapeutic agent for an ErbB2-overexpressing cancer.

Methods of the invention concern evaluating the potential efficacy of an ErbB2-targeting therapeutic agent for the treatment of cancer in a patient comprising evaluating the expression of PTEN in cells of the cancer. The term "ErbB2-targeting therapeutic agent" refers to a compound or composition that has a therapeutic application based on its ability to affect directly or indirectly ErbB2 expression or activity in a cell. "Potential efficacy" refers to possible therapeutic effectiveness of a therapeutic agent. It is contemplated that evaluating the expression of PTEN can involve, in some cases, comparing a level or amount observed in the cancer cells with a level of amount observed in noncancerous or normal cells or in cells that are not ErbB2-overexpressing cells. The term "evaluate" is used according to its plain and ordinary meaning to refer to "examine and judge carefully" or "consider."

A patient whose cancer cells have PTEN expression that is lower than PTEN expression in a normal (noncancerous) cell or in cancer cells expressing PTEN at levels similar to that in a normal cell (considered normal PTEN expression levels) is predictive of a patient more likely not to respond to (or be resistant to) an ErbB2 targeting agent than a patient whose PTEN expression is at a normal or above-normal level. It is contemplated that one or more standards may be generated in which a normal level of PTEN expression is defined or identified. That standard may then be referred to as a way of determining whether PTEN expression in a given patient is normal or below-normal. The type of standard generated will depend upon the assay or test employed to evaluate PTEN expression. In some embodiments of the invention, a score is assigned to a sample based on certain criteria and numbers within or below a certain number or range are deemed "below normal." In preferred embodiments, PTEN expression is considered below normal if an assay indicates that a particular measurement, amount or level is at about or at most about 80%, 75%, 70%, 65%, 60%, 55%, 50%, 45%, 40%, 35%, 30%, 25%, 20%, 15%, 10%, 5% or less of the measurement, amount or level observed in cells that have normal levels of PTEN expression. In other words, for example, a cell with normal PTEN expression exhibit a level of PTEN transcript that is x; the sample from the patient being tested may be 0.5x, in which case, in some embodiments that patient may be considered to have a below normal level of PTEN transcript and thus a below normal level of PTEN expression. Alternatively, in some embodiments, PTEN expression is considered below normal if an assay indicates that a particular measurement, amount or level is about or at least about 1, 2, 3, 4, 5, 6, 7, 8, 9, 10 or more standard deviations below the measurement, amount or level observed in cells that have normal levels of PTEN expression. In other cases, PTEN expression may be considered below normal if a measurement, amount or level indicative of PTEN expression is or is at most 2, 3, 4, 5, 6, 7, 8, 9, 10, 15, 20, 25, 30, 35, 40, 45, 50 or more times less than the measurement, amount, or level indicative of PTEN expression in normal cells.

Methods of the invention that involve evaluating the expression of PTEN in cancer cells can be achieved by a number of ways that directly or indirectly provide information regarding PTEN expression. Thus, ways of evaluating PTEN expression include, but are not limited to, assessing or measuring PTEN protein, assessing or measuring PTEN transcript, sequencing PTEN transcript or genomic sequence, measuring PTEN gene copy number, assaying PTEN gene methylation status, and assaying PTEN activity.

It is contemplated that methods and compositions of the invention could be implemented with respect to cancer patients, particularly to patients with ErbB2-overexpressing cancers. It is understood that the term "ErbB2-overexpressing cancer" refers to a cancer whose etiology or cause is believed to be related to cancer cells that express higher levels of ErbB2 protein compared to noncancerous cells or cancer cells whose etiology or cause is not related to ErbB2 protein levels. Therefore, in some embodiments of the invention, the cancer being treated involves cancerous cells of the breast, lung, ovary, brain, gastrointestinal tract, salivary duct, endometrium, prostate, head & neck, glioma, pancreas, hepatocyte, myeloma, soft tissue sarcoma, or non-small cell lung cancer, but is not limited to such.

The invention can be used with respect to any agent that targets ErbB2 so as to reduce, inhibit, eliminate, or ameliorate its activity. Such agents may work by directly affecting ErbB2 activity or they may work indirectly by affecting ErbB2 transcription, translation, post-translational modification, transcript or protein stability, transcript or protein localization, or some other mechanism that ultimately affects the amount of a protein's activity. In particular embodiments of the invention, the ErbB2-targeting therapeutic agent is trastuzumab, which is commercially known as Herceptin™.

In some embodiments, the expression of PTEN in cancer cells is evaluated by steps that include, but are not limited to, (a) obtaining from the patient a sample comprising cancer cells; and (b) determining the level of PTEN expression in the sample. Alternatively, the level or amount of PTEN expression in a particular patient may already be known, and consequently, that level or amount would be evaluated to make a determination regarding efficacy of a therapeutic agent in embodiments of the invention.

A sample from a patient refers to a biological sample, which includes, but is not limited to a tissue biopsy or section, blood sample, lavage, swab, scrape, nipple aspirate, or other composition that may be extracted from the body and that contains cancer cells. In particular embodiments, the present invention concerns a sample that contains all or part of a tissue biopsy. In further embodiments, the sample contains all or part of a breast tissue biopsy, which may be from a bilateral biopsy or a unilateral biopsy.

In some embodiments of the invention, methods involve evaluating PTEN expression in cancer cells by assessing PTEN protein, PTEN transcript, or PTEN gene copy number. The term "assessing" is used according to its ordinary and plain meaning to refer to "determining the extent of" In certain embodiments, PTEN protein or transcript is assessed by assaying (measuring) the amount of PTEN protein, transcript, or gene copy in the cancer cells. In specific aspects of the invention, PTEN expression is evaluated by assessing PTEN protein. An anti-PTEN antibody can be used in some cases to assess PTEN protein. Such methods may involve using immunohistochemistry, Western blotting, ELISA, immunoprecipitation, or an antibody array. In particular embodiments, PTEN protein is assessed using immunohistochemistry. The use of immunohistochemistry allows for quantitation and characterization of PTEN protein. It also allows an immunoreactive score for the sample to be determined. The term "immunoreactive score" (IRS) refers to a number that is calculated based on a scale reflecting the percentage of PTEN positive cells (on a scale of 1-4, where 0=0%, 1=<10%, 2=10%-50%, 3=>50%-80%, and 4=>80%) multiplied by the intensity of PTEN staining (on a scale of 1-3, where 1=weak, 2=moderate, and 3=strong). Immunoreactive scores range from 0-12.

In some embodiments of the invention, PTEN expression is evaluated by assessing PTEN transcription. PTEN transcription can be assessed by a variety of methods including those that involve amplifying PTEN transcripts or performing Northern blotting on PTEN transcripts. Amplification of PTEN transcripts can be utilized in quantitative polymerase chain reactions, which are well known to those of ordinary skill in the art. Alternatively, nuclease protection assays may be implemented to quantify transcripts. Other methods that take advantage of hybridization between a probe and target are also contemplated, such as fluorescence in situ hybridization (FISH) and RNA in situ hybridization (RISH).

Further embodiments of the invention involve evaluating PTEN expression by assaying the level of PTEN activity. PTEN is a phosphatase and its activity can be observed and measured using a phosphatase assay involving a PTEN substrate, such as PIP3, or measured indirectly by measuring Akt phosphorylation. Thus, the phosphorylation level of Akt can be determined or analyzed. Alternatively, when the level of PTEN activity is down, the level of the lipid PIP3 is relatively elevated. Thus, PTEN activity can be assayed by measuring the level of PIP3. Any other compound affected by PTEN activity can be evaluated as a way of assaying for PTEN activity.

In some embodiments of the invention, PTEN expression is determined by sequencing a PTEN transcript or PTEN genomic sequence or evaluating any modifications of such sequences. Sequencing can be done to determine whether there has been loss of heterozygosity (LOH) of the PTEN gene. Alternatively, sequencing can provide information regarding the nature of any mutations in the PTEN gene, such as deletions, insertions, frame-shifts, translocations, or truncations, which may result in mutations in the PTEN protein. Such mutations can affect PTEN expression and/or activity and thus are relevant to the claimed invention. Moreover, in some cases, modification of a PTEN-encoding sequence provides information regarding the level of PTEN expression or activity in a cell. Moreover, the occurrence of any epigenetic silencing of the PTEN genomic sequence can be evaluated. An example of such silencing involves methylation, and thus, in some methods of the invention, the evaluation of a PTEN genomic sequence involves determining whether one or both PTEN genes is methylated.

Assessment of PTEN expression, protein, sequence, transcript or activity may involve labels, tags, colorimetric indicators including fluorescence, enzyme indicators, radioactivity, or other means to quantify or characterize such levels or amounts.

In yet further aspects, compositions or methods of the invention may assess, detect, affect or result in the reduced phosphorylation of the PTEN polypeptide, thus assessing the phosphorylation state or increasing the activity of PTEN. In one aspect, trastuzumab may inhibit Src tyrosine kinase. Src activation has recently been reported to increase PTEN tyrosine phoshorylation (Lu et al., 2003). Therapeutic or diagnositc methods may inhibit or detect inhibition of Src kinase activity and reduced Src phosphorylation on Y416, an indicator of Src activity (Frame, 2002). Reduced Src-Y416 phosphorylation typically corresponds to reduced PTEN tyrosine phosphorylation. Reduced Src-Y416 phosphorylation may be assessed by using an antibody that specifically binds a phosphorylated tyrosine of PTEN. In other aspects, trastuzumab-mediated Src inhibition may be assessed by determining Src binding to ErbB2, which, for example, is inhibited by trastuzumab treatment. Trastuzumab may induce a reduction of ErbB2 bound Src, indicating that trastuzumab inhibited Src activity in ErbB2 overexpressing cells most likely by inhibiting Src binding to ErbB2.

Src kinase inhibitors, such as PP2, may reduce PTEN tyrosine phosphoryulation in the ErbB2-overexpressing breast cancer cells (Yu et al., 1998a). These inhibitors may be used in combination with other methods and compositions of the invention for assessment or regulation of PTEN status in a cell or subject of interest. For example, PP2 treatment may effectively inhibited Src phosphorylation on Y416 and also dramatically reduced tyrosine phosphorylation of PTEN, similar to trastuzumab's effect. Trastuzumab treatment inhibits Src binding to ErbB2 in breast cancer cells, thus inhibiting Src kinase activity, which leads to reduced PTEN tyrosine phosphorylation and increased PTEN membrane localization and activity.

Methods of the invention also include, in some embodiments, a step of administering the ErbB2 targeting therapeutic agent to the patient. Such a step is particularly contemplated after it has been determined that there is potential efficacy for the agent in a particular patient. In certain embodiments, the therapeutic agent is trastuzumab. In others it can be inhibitors of PI3K family proteins. Thus, it is contemplated that another agent for use with the invention is LY294002 and/or Wortmannin, which inhibit PI3K. In other cases, the patient can be given a composition comprising any combination of trastuzumab, LY294002, and Wortmannin. Furthermore, methods can also involve treating the patient with other anti-cancer therapy, which can be selected from the group consisting of radiotherapy, chemotherapy, immune therapy, or gene therapy.

Other methods of the invention include a method for evaluating potential efficacy of a therapeutic agent for the treatment of an ErbB2-overexpressing cancer comprising: (a) obtaining from the patient a sample comprising cancer cells; (b) evaluating the level of PTEN expression or activity in the sample. In some cases, the ErbB2-overexpressing cancer is breast cancer. In other embodiments, the therapeutic agent is trastuzumab.

The present invention also concerns kits for evaluating potential efficacy of an anti-cancer agent for the treatment of breast cancer. In some embodiments, the kits include (a) an ErbB2 reagent for evaluating the level of ErbB2 expression or activity in a sample; (b) a PTEN reagent for evaluating the level of PTEN expression or activity in a sample. It is contemplated that the reagents for evaluating the level of expression or activity of either ErbB2 or PTEN can be one or more nucleic acids. The nucleic acids may be complementary to all or part of ErbB2 or PTEN and they can be used in hybridization reactions, such as for amplification (primers), primer extensions, nuclease protection assays, Northern blotting, or with an array or other structure. Alternatively, antibodies against either ErbB2 or PTEN can be used, for example, in Western blotting, ELISAs, other sandwich assays, antibody arrays, immunohistochemistry, or FACS analysis. The antibody may be a monoclonal or a polyclonal antibody. In other embodiments, the kit comprises a ErbB2 and/or PTEN reagent that is an ErbB2 nucleic acid or PTEN nucleic acid. The term "PTEN nucleic acid" refers to a nucleic acid that is complementary or identical to all or part of a PTEN nucleic acid sequence in order to identify or detect specifically the PTEN nucleic acid, as opposed to other nucleic acids. Likewise is the case for a "ErbB2 nucleic acid." Such nucleic acids may be further characterized as discussed herein. It is contemplated that kits of the invention may comprise 1, 2, 3, 4, 5, 6 or more ErbB2 reagents and 1, 2, 3, 4, 5, 6 or more PTEN reagents.

While the present invention is discussed with respect to the treatment of cancer, it is contemplated that the present invention has applications generally to any disease or condition involving ErbB2 activity, particularly any diseases or conditions characterized by a relatively high activity or expression level of ErbB2. Furthermore, any method used or discussed herein with respect to the detection of ErbB2 overexpression in cancer cells may be implemented with respect to the detection of PTEN expression, and vice versa.

It is specifically contemplated that any embodiment of any method or composition of the invention may be used with respect to any other method or composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A: Immunoblotting (IB) of ErbB2, Tyr1248-phosphorylated ErbB2 (p-ErbB2), phosphorylated Akt (p-Akt), and total Akt in trastuzumab (+, 2 µg/ml) or control IgG-treated (−, 2 µg/ml) BT474 cells and SKBr3 cells. β-actin blot served as loading controls in all IB experiments. All in vitro experiments were repeated at least three times. Reproducible representative results are shown. FIG. 1B: PI3K assay after 2 µg/ml of trastuzumab treatment of SKBr3 cells for the indicated time. Lysates were immunoprecipitated with the PY20 antibody followed by incubation in kinase buffer. Numbers below the panel indicate relative PI3K activity to untreated cells. IP with IgG served as a control. FIG. 1C: Trastuzumab transiently increased association of the p85 subunit of PI3K with the ErbB2 complex. ErbB2 immunoprecipitates and total cell lysates from untreated or trastuzumab-treated (2 µg/ml) cells were immunoblotted with indicated antibodies. FIG. 1D: Increased PTEN phosphatase activities in trastuzumab-treated (2 µg/ml) SKBr3 cells. Upper right insert shows, from left to right, immunoprecipitated PTEN proteins from untreated and trastuzumab-treated (20 or 60 min) cells. Immunoprecipitates by rabbit IgG from trastuzumab treated cells were the negative control. FIG. 1E: Trastuzumab increased membrane bound PTEN in BT474 cells. PTEN protein in the cytosolic pool (sol) and the membrane bound pool (mem) of untreated (−) or trastuzumab-treated (+, 2 µg/ml) cell lysates were blotted with indicated antibodies. E-cadherin and ErbB2 were membrane protein markers. FIG. 1F: Reduction of PTEN tyrosine phosphorylation after trastuzumab treatment in BT474 cells. BT474 cells were treated without or with 2 µg/ml of trastuzumab for the indicated time. PTEN IP using the A2B1 PTEN antibody was followed by IB with PY99 phosphotyrosine antibody (top). The membrane was then stripped and reprobed with A2B1 PTEN antibody to show the IP efficiency. IgG was used as a negative control. Numbers below the panel indicate relative levels of PTEN tyrosine phosphorylation with 0 min trastuzumab treatment defined as 1.

FIG. 2A: Immunofluorescent flow cytometry analysis of ErbB2 on the cell membrane. BT474 and SKBR3 human breast cancer cells were treated for 1 h and 15 h with 2 mg/ml trastuzumab. After washing cells with PBS buffer, membrane-localized ErbB2 was detected with anti-ErbB2 antibody (Ab5, Calbiochem, La Jolla, Calif.), which recognizes the extracellular domain of ErbB2, followed by FITC-conjugated secondary antibody. The shaded and unshaded areas represent the distribution of ErbB2 in trastuzumab-treated and untreated cells, respectively. The upper right percentage indicates the number of ErbB2 receptors on the membrane in trastuzumab-treated cells as the percentage of those in untreated cells. FIG. 2B: Immunofluorescence staining of ErbB2 in SKBR3 cells. The cells were plated into glass chambers. After 24 h, the cells were treated for 1 h with 2 mg/ml trastuzumab, fixed with 4% paraformaldehyde, and were perforated with 0.3% TritonX/PBS. ErbB2 protein was probed with anti-ErbB2 antibody (Ab3) and FITC-conjugated secondary antibody.

FIG. 3A: PTEN protein is reduced in SKBr3 cells transfected with PTEN AS (25 nM) compared to mock or mismatched (MIS) oligonucleotidetransfected cells. FIG. 3B: Trastuzumab-mediated Akt dephosphorylation is attenuated in PTEN AS-transfected SKBr3 cells. MIS or PTEN AS-transfected SKBr3 cells (as in FIG. 3A) were treated with trastuzumab (2 µg/ml) for the indicated times, and cell lysates were immunoblotted. FIG. 3C: Trastuzumab inhibited cell proliferation less in PTEN AS-treated SKBr3 cells compared to MIS transfected cells. MIS or PTEN AS-transfected SKBr3 cells (as in FIG. 3A) were treated with trastuzumab (2 µg/ml) for 3 and 5 days. Cell mass was determined by MTS assay. Percent cell number represents % cell counts under each treatment relative to untreated cells. FIG. 3D: Similar cell growth in MIS- or PTEN AS-transfected SKBr3 cells without trastuzumab. Percent cell numbers represents % cell counts compared to Day 1 (defined as 100%). FIG. 3E: PTEN-reduced BT474 cells are more resistant to trastuzumab plus paclitaxel than PTEN normal cells but have a similar paclitaxel response to PTEN normal cells. BT474 cells were transfected with 25 nM MIS or PTEN AS, treated by paclitaxel (1, 2, and 4 nM) without or with 2 µg/ml of trastuzumab (Ttzm) for 3 days. Percent cell viability are cell mass as a % of untreated MIS-transfected cells. FIG. 3F: PTEN expression is reduced in BT474 xenografts injected with PTEN AS. BT474 cells were inoculated into the mfp of female nude mice. After tumors reached 150 mm3, MIS or PTEN AS were injected intratumor (15 µg/injection, twice a week) for 1 week. Removed tumors were stained with antibodies to PTEN and ErbB2. FIG. 3G: PTEN-deficient BT474 xenografts are more resistant to trastuzumab than PTEN normal BT474 xenografts. After 1 week of PTEN AS or MIS treatment (as in FIG. 3F), mice were treated with trastuzumab (10 mg/kg) or vehicle twice a week. The arrows indicate the starting days of AS/MIS treatment (AS) and trastuzumab/vehicle treatment (Ttzm). The results shown are the mean tumor volume+SE; *p<0.05.

FIG. 4A: BT474 cells were treated with PTEN AS or MIS Control oligonucleotides plated on glass chamber slides, and incubated overnight with 2 mg/ml of trastuzumab for 48 h. The cells were then incubated with 10 mM of BrdU for 30 min, fixed with ethanol, and incubated with anti-BrdU antibody following the manufacturer's protocol (Cell Proliferation ELISA, BrdU colorimetric kit, (Roche Molecular Biochemicals, Indianapolis, Ind.). BrdU-positive cells were visualized under an immunofluorescence microscope. Cells were counterstained with DAPI as a control. FIG. 4B: BrdU positivity in BT474 cells were counted and compared with total cell numbers determined by DAPI positive cells. The results shown are representative of three repeated experiments.

FIG. 5A: BT474 cells were treated with MIS or PTEN AS oligonucleotides as FIG. 3A. Cells were then treated with trastuzumab (Ttzm, 2 µg/ml), LY294002 (LY, 0.8 µM), or trastuzumab plus LY294002 (Ttzm+LY) for 3 days. Percent inhibition is % growth reduction under each treatment relative to untreated cells. **p<0.01. FIG. 5B:

BT474 cells were treated with MIS or PTEN AS as in FIG. 3A. Cells were then treated with trastuzumab (2 µg/ml), Wortmannin (WN, 1 µM), or tras-tuzumab plus Wortmannin (Ttzm+WN) for 3 days. Percent inhibition is % growth reduction under each treatment relative to untreated cells. **p<0.01. FIG. 5C: BT474 xenografts were treated with PTEN AS as in FIG. 3G. Mice were treated with trastuzumab (10 mg/kg) twice a week or/and LY294002 (100 mg/kg) 3 times a week for 3 weeks. The arrows indicate the starting days of AS treatment (AS) and trastuzumab and/or LY294002 treatment (Ttzm, LY). The results are the mean tumor volume+SE. *p<0.05.

FIGS. 6A-6D. Patients with PTEN deficient breast tumors have a poor response to trastuzumab-based therapy. FIG. 6A: PTEN expression patterns in human breast tumors. Forty-seven ErbB2-overexpressing (3+, 2+, and/or FISH positive) primary breast carcinomas were collected from patients who subsequently developed metastatic breast cancer and received trastuzumab plus taxane chemotherapy (paclitaxel or docetaxel) in clinical trials conducted (Esteva et al., 2002; Seidman et al., 2001). PTEN expression in these tumors was examined by immunohistochemistry and semi-quantified using immunoreactive scores (IRS). IRS was calculated by the percent of PTEN positive cells (0%=0, <10%=1, 10%-50%=2, 51%-80%=3, >80%=4) multiplied by the intensity of the staining (weak=1, moderate=2, strong=3), resulting in IRS ranging from 0-12. Representative PTEN staining (IRS 12, 9, 3, and 0) of tumor samples was shown. FIG. 6B: Worse responses to trastuzumab-based therapy in patients with PTEN low and negative tumors than those with PTEN positive tumors. PTEN low and negative tumors were defined by PTEN IRS <9 (left panel), or <4 (right panel). *, P<0.05; , P<0.01. Complete response (CR), partial response (PR), stable disease (SD), and progressive disease (PD), number of patients studied (n). FIG. 6C: Trastuzumab plus taxane response rates in patients with ErbB2 FISH positive and/or IHC 3+ ErbB2 overexpression breast cancers versus patients with ErbB2 FISH negative and/or 2+ ErbB2 overexpression cancers (P>0.05). FIG. 6D: Among patients with ErbB2 FISH positive and/or IHC 3+ ErbB2 overexpressing breast cancers, patients with PTEN low and negative tumors responded less to trastuzumab-based therapy than those with PTEN positive tumors (, P<0.01). Data in FIGS. 4A-4D were obtained in a double blind manner.

DESCRIPTION OF ILLUSTRATIVE EMBODIMENTS

Figure 1A:
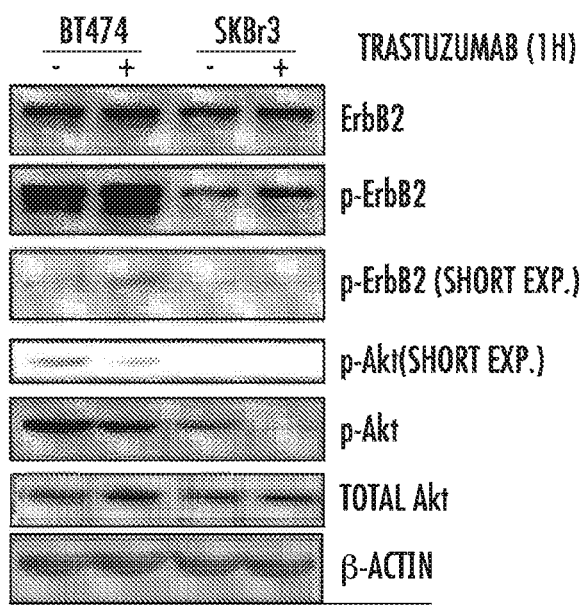
FIGS. 1A-1F. Rapid Akt dephosphorylation and PTEN activation by trastuzumab

The present invention concerns methods and kits for evaluating or determining the potential efficacy of an ErbB2 targeting agent in a patient who may be given the agent for the treatment of an ErbB2-overexpressing disease such as cancer. More particularly, the invention concerns evaluating PTEN expression or activity in cancer cells of the patient in order to predict whether the patient will be resistant to the ErbB2 targeting agent. In addition to diagnostic applications, the present invention concerns therapeutic and prognostic applications

I. PTEN

PTEN (phosphatase and tensin homologue, also named MMAC1/TEP) is a dual phosphatase that mainly dephosphorylates position D3 of membrane phosphatidylinositol-3,4,5 trisphosphate (PI3,4,5P3), which is the site for recruiting the pleckstrin-homology domain of Akt to the cell membrane (Cantley and Neel, 1999; Parsons and Simpson, 2003; Vivanco and Sawyers, 2002). Since the phosphatidylinositol 3-Kinase (PI3K) catalyzes the production of PI3,4,5P3 (Cantley, 2002), PTEN antagonizes this PI3K function and negatively regulates Akt activities. Loss of PTEN function due to PTEN mutations, PTEN haploinsufficiency from LOH at the PTEN locus, and epigenetic down-modulation of PTEN have been reported in nearly 50% of breast cancers and in many other cancer types (Li et al., 1997; Mutter et al., 2000; Parsons and Simpson, 2003; Teng et al., 1997; Whang et al., 1998). Restoration of PTEN expression in PTEN-null cells leads to inhibition of Akt activities and tumor suppression (Li and Sun, 1998; Lu et al., 1999). Therefore, PTEN is an important tumor suppressor gene. However, possible functional interactions of PTEN activity with ErbB2 receptor tyrosine kinase signaling and potential roles of PTEN in the anti-tumor activity of trastuzumab have never been explored.

The nucleic acid and amino acid sequences for human PTEN can be found at GenBank Accession number U93051 and AAC51183, respectively, which are specifically incorporated herein by reference.

II. Erbb2 and Erbb2 Targeting Agents

ErbB2 is a polypeptide also known as HER2 (Human Epidermal growth factor Receptor 2), which is encoded by a proto-oncogene referred to as c-erbB2, HER2, or HER2/neu. It is overexpressed as a result of a gene amplification in about 25% of breast cancers (Slamon et al., 1989). Patients are evaluated to determine whether they overexpress ErbB2. This can be accomplished by several ways including the use of the DAKO HercepTest™, an immunohistochemical test for detecting ErbB2 protein overexpression, or the Vysis PathVysion™ HER2DNA Probe, a FISH test for detecting ErbB2 gene amplification.

A therapeutic regimen of trastuzumab (Herceptin) in combination with paclitaxel is generally indicated for treatment of patients with metastatic breast cancer whose tumors overexpress the ErbB2 protein and who have not received chemotherapy for their metastatic disease. Trastuzumab is a humanized anti-ErbB2 monoclonal antibody, and thus, it qualifies as an ErbB2 targeting agent. Because the present invention concerns ErbB2-overexpressing cancers, it has applications with respect to any agent used to target ErbB2, and should not be limited to evaluating resistance to trastuzumab.

III. Proteinaceous Compositions

The present invention concerns evaluating the expression and/or activity of the polypeptide PTEN, as well as determining whether a cancer is a ErbB2-overexpressing cancer.

As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may be at least, at most or may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 582, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater amino molecule residues, and any range derivable therein. It is specifically contemplated that such lengths of contiguous amino acids from SEQ ID NO:2 (amino acid sequence of human PTEN) are part of the invention.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases found on the internet at the National Institutes of Health website. The coding regions for these known genes may be amplified and/or expressed using the techniques disclosed herein or as would be know to those of ordinary skill in the art. Alternatively, various commercial preparations of proteins, polypeptides and peptides are known to those of skill in the art.

When the present application refers to the function or activity of PTEN, it is meant that the molecule in question has at least the ability to catalyze the dephosphorylation of another polypeptide. Determination of which molecules possess this activity and what level of activity there is may be achieved using assays familiar to those of skill in the art, and include those described in the Examples.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

Another embodiment of the present invention are antibodies. In some cases, the antibody is an ErbB2 targeting agent, while in others, it is used to evaluate, assess, or determine PTEN or ErbB2 expression. It is understood that antibodies can be used to quantify polypeptides. Such antibodies, polyclonal or monoclonal, can be generated. Means for preparing and characterizing antibodies are also well known in the art (See, e.g., Harlow and Lane, 1988; incorporated herein by reference). Alternatively, they can be obtained commercially. For example, PTEN antibodies can be readily obtained from Santa Cruz Biotechnology (A2B1, Santa Cruz, Calif.) and Lab Vision Corp. (Ab-2, Fremont, Calif.).

As discussed, in some embodiments, the present invention concerns immunodetection methods for assessing, evaluating, determining, quantifying and/or otherwise detecting biological components such as PTEN polypeptides.

Immunodetection methods include enzyme linked immunosorbent assay (ELISA), radioimmunoassay (RIA), immunoradiometric assay, fluoroimmunoassay, chemiluminescent assay, bioluminescent assay, western blot, and screening an antibody array, though several others are well known to those of ordinary skill. The steps of various useful immunodetection methods have been described in the scientific literature, such as, e.g., Doolittle et al., 1999; Gulbis and Galand, 1993; De Jager et al., 1993; and Nakamura et al., 1987, each incorporated herein by reference.

In general, the immunobinding methods include obtaining a sample suspected of containing a protein, polypeptide and/or peptide, and contacting the sample with a first antibody, monoclonal or polyclonal, in accordance with the present invention, as the case may be, under conditions effective to allow the formation of immunocomplexes.

The immunobinding methods include methods for detecting and quantifying the amount of an antigen component in a sample and the detection and quantification of any immune complexes formed during the binding process. Here, one would obtain a sample suspected of containing an antigen or antigenic domain, and contact the sample with an antibody against the antigen or antigenic domain, and then detect and quantify the amount of immune complexes formed under the specific conditions.

In terms of antigen detection, the biological sample analyzed may be any sample that is suspected of containing an antigen or antigenic domain, such as, for example, a cancer cell or tissue, or any biological fluid that comes into contact with the cell or tissue, including blood and/or serum.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

One method of immunodetection designed by Charles Cantor uses two different antibodies (see, Sano et al., 1992). A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, for example, with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR™ method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR™ reaction with suitable primers with appropriate controls. At least in theory, the enormous amplification capability and specificity of PCR™ can be utilized to detect a single antigen molecule.

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

The antibodies of the present invention may also be used in conjunction with both fresh-frozen and/or formalin-fixed, paraffin-embedded tissue blocks prepared for study by immunohistochemistry (IHC). For example, immunohistochemistry may be utilized to characterize PTEN or to evaluate the amount PTEN in a cell. The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990). Other details are provided in the Examples section.

IV. PTEN Nucleic Acids

The present invention concerns polynucleotides and oligonucleotides, isolatable from cells, that are free from total genomic DNA and that are capable of expressing all or part of a protein or polypeptide. The polynucleotides or oligonucleotides may be identical or complementary to all or part of a nucleic acid sequence encoding a PTEN amino acid sequence. These nucleic acids may be used directly or indirectly to assess, evaluate, quantify, or determine PTEN expression.

As used in this application, the term "PTEN polynucleotide" refers to a PTEN-encoding nucleic acid molecule that has been isolated essentially or substantially free of total genomic nucleic acid to permit hybridization and amplification, but is not limited to such. Therefore, a "polynucleotide encoding PTEN" refers to a DNA segment that contains wild-type (SEQ ID NO:1), mutant, or polymorphic PTEN polypeptide-coding sequences isolated away from, or purified free from, total mammalian or human genomic DNA. A PTEN oligonucleotide refers to a nucleic acid molecule that is complementary or identical to at least 5 contiguous nucleotides of a PTEN-encoding sequence, such as SEQ ID NO:1, which is the cDNA sequence encoding human PTEN.

It also is contemplated that a particular polypeptide from a given species may be represented by natural variants that have slightly different nucleic acid sequences but, nonetheless, encode the same protein.

Similarly, a polynucleotide comprising an isolated or purified wild-type, polymorphic, or mutant polypeptide gene refers to a DNA segment including wild-type, polymorphic, or mutant polypeptide coding sequences and, in certain aspects, regulatory sequences, isolated substantially away from other naturally occurring genes or protein encoding sequences. In this respect, the term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. A nucleic acid encoding all or part of a native or modified polypeptide may contain a contiguous nucleic acid sequence encoding all or a portion of such a polypeptide of the following lengths: about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including such sequences from SEQ ID NO:1, other PTEN encoding sequences, or ErbB2-encoding sequences.

In particular embodiments, the invention concerns isolated DNA segments and recombinant vectors incorporating DNA sequences that encode all or part of a wild-type, polymorphic, or mutant PTEN polypeptide or peptide that includes within its amino acid sequence a contiguous amino acid sequence in accordance with, or essentially corresponding to a native polypeptide. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

In other embodiments, the invention concerns isolated DNA segments and recombinant vectors incorporating DNA sequences that encode a polypeptide or peptide that includes within its amino acid sequence a contiguous amino acid sequence in accordance with, or essentially corresponding to the polypeptide.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

The sequence of a PTEN polypeptide will substantially correspond to a contiguous portion of that shown in SEQ ID NO:2, and have relatively few amino acids that are not identical to, or a biologically functional equivalent of, the amino acids shown in SEQ ID NO:2. The term "biologically functional equivalent" is well understood in the art and is further defined in detail herein.

Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2 will be sequences that are "essentially as set forth in SEQ ID NO:2."

In certain other embodiments, the invention concerns isolated DNA segments and recombinant vectors that include within their sequence a contiguous nucleic acid sequence from that shown in SEQ ID NO:1. This definition is used in the same sense as described above and means that the nucleic acid sequence substantially corresponds to a contiguous portion of that shown in SEQ ID NO:1 and has relatively few codons that are not identical, or functionally equivalent, to the codons of SEQ ID NO:1. The term "functionally equivalent codon" is used herein to refer to codons that encode the same amino acid, such as the six codons for arginine or serine, and also refers to codons that encode biologically equivalent amino acids.

The various probes and primers designed around the nucleotide sequences of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

It also will be understood that this invention is not limited to the particular nucleic acid and amino acid sequences of SEQ ID NO:1 and SEQ ID NO:2 respectively. Recombinant vectors and isolated DNA segments may therefore variously include the PTEN-coding regions themselves, coding regions bearing selected alterations or modifications in the basic coding region, or they may encode larger polypeptides that nevertheless include PTEN-coding regions or may encode biologically functional equivalent proteins or peptides that have variant amino acids sequences.

Moreover, the nucleic acids are not limited to coding sequences. In some embodiments of the invention, genomic PTEN sequences can be used to determine directly or indirectly PTEN expression.

Encompassed by certain embodiments of the present invention are DNA segments encoding relatively small peptides, such as, for example, peptides of from about 15 to about 50 amino acids in length, and more preferably, of from about 15 to about 30 amino acids in length; and also larger polypeptides up to and including proteins corresponding to the full-length sequences set forth in SEQ ID NO:2, or to specific fragments of SEQ ID NO:1 that correspond to differences as compared to the published sequence for human PTEN.

Nucleic acid molecules may be comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (2001) and Ausubel et al. (1996), both incorporated herein by reference. In addition to encoding a modified polypeptide such as modified gelonin, a vector may encode non-modified polypeptide sequences such as a tag or targetting molecule. In addition to control sequences that govern transcription and translation, vectors and expression vectors may contain nucleic acid sequences that serve other functions as well. Such sequences may include one or more of the following: promoters, enhancers, initiation signals, internal ribosome binding sites, multiple cloning sites, splicing sites, termination signals, polyadenylation signals, origins of replication, and selectable and screenable markers.

The nucleic acid sequences disclosed herein have a variety of uses as probes or primers for embodiments involving nucleic acid hybridization in methods of the invention.

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Such probes or primers can be of lengths described above from SEQ ID NO:1. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to a nucleic acid corresponding to SEQ ID NO:1 or other PTEN nucleic acid sequence are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 2001). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety. Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

Following any amplification or step such as primer extension, it may be desirable to separate the amplification or primer extension product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

Other methods involve fluorescent in situ hybridization (FISH), which refers to process that vividly paints chromosomes or portions of chromosomes with fluorescent molecules. Such techniques are well known to those of skill in the art (Weier et al., 2002; Moter et al., 2000; Nath et al., 1998). Another method that may also be employed involves RNA in situ hybridization (RISH). This technique may utilize nonradioactive probes such as digoxigenin-labeled copy RNA (cRNA) probes for the examination of mRNA expression, and is well known to one of ordinary skill in the art.

Reverse transcription (RT) of RNA to cDNA followed by relative quantitative PCR™ (RT-PCR) can be used to determine the relative concentrations of specific mRNA species isolated from a cell, such as a PTEN-encoding transcript. By determining that the concentration of a specific mRNA species varies, it is shown that the gene encoding the specific mRNA species is differentially expressed.

Specifically contemplated are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al., 1991). It is contemplated that this technology may be used in conjunction with evaluating the expression level of PTEN with respect to diagnostic methods of the invention.

V. Combination Treatments

The compounds and methods of the present invention may be used in the context of cancer and other diseases and conditions that are caused or aggravated by ErbB2 overexpression. In order to increase the effectiveness of a treatment with the compositions of the present invention, such as trastuzumab, it may be desirable to combine these compositions with other agents effective in the treatment of those diseases and conditions. For example, the treatment of a cancer may be implemented with therapeutic compounds of the present invention and other anti-cancer therapies, such as anti-cancer agents or surgery.

Various combinations may be employed; for example, where the ErbB2 targeting agent is "A" and the secondary anti-cancer therapy is "B" as follows:

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the ErbB2 targeting agent to a patient will follow general protocols for the administration of that particular secondary therapy, taking into account the toxicity, if any, of the ErbB2 targeting agent. It is expected that the treatment cycles would be repeated as necessary. It also is contemplated that various standard therapies, as well as surgical intervention, may be applied in combination with the described cancer therapy.

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with an expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes an expression construct and the other includes a second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that ErbB2 targeting therapy could be used similarly in conjunction with chemotherapeutic, radiotherapeutic, immunotherapeutic or other biological intervention, in addition to other pro-apoptotic or cell cycle regulating agents.

Alternatively, the ErbB2 targeting therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

A. Chemotherapy

Cancer therapies also include a variety of combination therapies with both chemical and radiation based treatments. The use of trastuzumab has been employed with paclitaxel, or anthracyclines and cyclophosphamide. It is contemplated that other combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy.

B. Radiation Therapy

Other factors that cause DNA damage and that have been used extensively generally for cancer include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. Trastuzumab is such an example. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with trastuzumab or another antibody to ErbB2 may be employed. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor such as mda-7 has been shown to enhance anti-tumor effects (Ju et al., 2000).

As discussed earlier, examples of immunotherapies currently under investigation or in use are immune adjuvants e.g., *Mycobacterium bovis, Plasmodium falciparum*, dinitrochlorobenzene and aromatic compounds (U.S. Pat. No. 5,801,005; U.S. Pat. No. 5,739,169; Hui and Hashimoto, 1998; Christodoulides et al., 1998), cytokine therapy e.g., interferons α, β and γ; IL-1, GM-CSF and TNF (Bukowski et al., 1998; Davidson et al., 1998; Hellstrand et al., 1998) gene therapy e.g., TNF, IL-1, IL-2, p53 (Qin et al., 1998; Austin-Ward and Villaseca, 1998; U.S. Pat. No. 5,830,880 and U.S. Pat. No. 5,846,945) and monoclonal antibodies e.g., anti-ganglioside GM2, anti-HER-2, anti-p185; Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). Combination therapy of cancer with herceptin and chemotherapy has been shown to be more effective than the individual therapies. Thus, it is contemplated that one or more anti-cancer therapies may be employed with the ErbB2 targeting therapies described herein.

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie and Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anticarbohydrate antibodies.

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated anigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

D. Gene Therapy

In yet another embodiment, the secondary treatment is a gene therapy in which a therapeutic polynucleotide is administered before, after, or at the same time as an ErbB2 targeting agent is administered. Delivery of an ErbB2 targeting agent in conjunction with a vector encoding one of the following gene products may have a combined anti-hyperproliferative effect on target tissues. A variety of proteins are encompassed within the invention, some of which are described below. Table 1 lists various genes that may be targeted for gene therapy of some form in combination with the present invention.

1. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA or siRNA directed to a particular inducer of cellular proliferation is used to prevent expression of the inducer of cellular proliferation.

The proteins FMS and ErbA are growth factor receptors, like ErbB. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

2. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, mda-7, FHIT, p16 and C-CAM can be employed.

In addition to p53, another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit, the $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes, $p16^B$, p19, $p21^{WAF1}$ and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zacl, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

3. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_{S,\ Mcl}$-1, A1, Bfl-1) or counteract Bcl-2 function and promote cell death (e.g., Bax, Bak, Bik, Bim, Bid, Bad, Harakiri).

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents.

Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Apo2 ligand (Apo2L, also called TRAIL) is a member of the tumor necrosis factor (TNF) cytokine family. TRAIL activates rapid apoptosis in many types of cancer cells, yet is not toxic to normal cells. TRAIL mRNA occurs in a wide variety of tissues. Most normal cells appear to be resistant to TRAIL's cytotoxic action, suggesting the existence of mechanisms that can protect against apoptosis induction by TRAIL. The first receptor described for TRAIL, called death receptor 4 (DR4), contains a cytoplasmic "death domain"; DR4 transmits the apoptosis signal carried by TRAIL. Additional receptors have been identified that bind to TRAIL. One receptor, called DR5, contains a cytoplasmic death domain and signals apoptosis much like DR4. The DR4 and DR5 mRNAs are expressed in many normal tissues and tumor cell lines. Recently, decoy receptors such as DcR1 and DcR2 have been identified that prevent TRAIL from inducing apoptosis through DR4 and DR5. These decoy receptors thus represent a novel mechanism for regulating sensitivity to a pro-apoptotic cytokine directly at the cell's surface. The preferential expression of these inhibitory receptors in normal tissues suggests that TRAIL may be useful as an anticancer agent that induces apoptosis in cancer cells while sparing normal cells. (Marsters et al., 1999).

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

TABLE 1

| Oncogenes | | | |
|---|---|---|---|
| Gene | Source | Human Disease | Function |
| Growth Factors | | | |
| HST/KS | Transfection | | FGF family member |
| INT-2 | MMTV promoter Insertion | | FGF family member |
| INTI/WNTI | MMTV promoter Insertion | | Factor-like |
| SIS | Simian sarcoma virus | | PDGF B |
| Receptor Tyrosine Kinases | | | |
| ERBB/HER | Avian erythroblastosis Virus; ALV promoter Insertion; amplified Human tumors | Amplified, deleted Squamous cell Cancer; glioblastoma | EGF/TGF-α/ Amphiregulin/ Hetacellulin receptor |
| ERBB-2/NEU/HER-2 | Transfected from rat Glioblastomas | Amplified breast, Ovarian, gastric cancers | Regulated by NDF/ Heregulin and EGF- Related factors |
| FMS | SM feline sarcoma virus | | CSF-1 receptor |
| KIT | HZ feline sarcoma virus | | MGF/Steel receptor Hematopoieis |

TABLE 1-continued

| | Oncogenes | | |
|---|---|---|---|
| Gene | Source | Human Disease | Function |
| TRK | Transfection from Human colon cancer | | NGF (nerve growth Factor) receptor |
| MET | Transfection from Human osteosarcoma | | Scatter factor/HGF Receptor |
| RET | Translocations and point mutations | Sporadic thyroid cancer; familial medullary thyroid cancer; multiple endocrine neoplasias 2A and 2B | Orphan receptor Tyr Kinase |
| ROS | URII avian sarcoma Virus | | Orphan receptor Tyr Kinase |
| PDGF receptor | Translocation | Chronic Myelomonocytic Leukemia | TEL (ETS-like transcription factor)/ PDGF receptor gene Fusion |
| TGF-β receptor | | Colon carcinoma mismatch mutation target | |
| NONRECEPTOR TYROSINE KINASES | | | |
| ABL | Abelson Mul. V | Chronic myelogenous leukemia translocation with BCR | Interact with RB, RNA polymerase, CRK, CBL |
| FPS/FES | Avian Fujinami SV; GA FeSV | | |
| LCK | Mul. V (murine leukemia Virus) promoter Insertion | | Src family; T cell signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES | | | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS Pathway |
| MISCELLANEOUS CELL SURFACE | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and *Drosophilia* homology | Nevoid basal cell cancer syndrome (Gorline syndrome) | 12 transmembrane domain; signals through Gli homogue CI to antagonize hedgehog pathway |
| TAN-1 Notch homologue | Translocation | T-ALL | Signaling |
| MISCELLANEOUS SIGNALING | | | |
| BCL-2 | Translocation | B-cell lymphoma | Apoptosis |
| CBL | Mu Cas NS-1 V | | Tyrosine- Phosphorylated RING finger interact Abl |
| CRK | CT1010 ASV | | Adapted SH2/SH3 interact Abl |
| DPC4 | Tumor suppressor | Pancreatic cancer | TGF-β-related signaling Pathway |
| MAS | Transfection and Tumorigenicity | | Possible angiotensin Receptor |
| NCK | | | Adaptor SH2/SH3 |
| GUANINE NUCLEOTIDE EXCHANGERS AND BINDING PROTEINS | | | |
| BCR | | Translocated with ABL in CML | Exchanger; protein Kinase |

TABLE 1-continued

| | Oncogenes | | |
|---|---|---|---|
| Gene | Source | Human Disease | Function |
| DBL | Transfection | | Exchanger |
| GSP | | | |
| NF-1 | Hereditary tumor Suppressor | Tumor suppressor neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS | | | |
| BRCA1 | Heritable suppressor | Mammary cancer/ovarian cancer | Localization unsettled |
| BRCA2 | Heritable suppressor | Mammary cancer | Function unknown |
| ERBA | Avian erythroblastosis Virus | | Thyroid hormone receptor (transcription) |
| ETS | Avian E26 virus | | DNA binding |
| EVII | MuLV promotor Insertion | AML | Transcription factor |
| FOS | FBI/FBR murine osteosarcoma viruses | | Transcription factor with c-JUN |
| GLI | Amplified glioma | Glioma | Zinc finger; cubitus interruptus homologue is in hedgehog signaling pathway; inhibitory link PTC and hedgehog |
| HMGI/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL Trithorax-like gene | Acute myeloid leukemia | Gene fusion of DNA-binding and methyl transferase MLL with ELI RNA pol II elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin regulation; interact RB?; regulate apoptosis? |
| N-MYC | Amplified | Neuroblastoma | |
| L-MYC | | Lung cancer | |
| REL | Avian Retriculoendotheliosis Virus | | NF-κB family transcription factor |
| SKI | Avian SKV770 Retrovirus | | Transcription factor |
| VHL | Heritable suppressor | Von Hippel-Landau syndrome | Negative regulator or elongin; transcriptional elongation complex |
| WT-1 | | Wilm's tumor | Transcription factor |
| CELL CYCLE/DNA DAMAGE RESPONSE | | | |
| ATM | Hereditary disorder | Ataxia-telangiectasia | Protein/lipid kinase homology; DNA damage response upstream in P53 pathway |
| BCL-2 | Translocation | Follicular lymphoma | Apoptosis |
| FACC | Point mutation | Fanconi's anemia group C (predisposition leukemia | |
| FHIT | Fragile site 3p14.2 | Lung carcinoma | Histidine triad-related diadenosine 5',3''''-$P^1.p^4$ tetraphosphate asymmetric hydrolase |
| hMLI/MutL | | HNPCC | Mismatch repair; MutL Homologue |

TABLE 1-continued

Oncogenes

| Gene | Source | Human Disease | Function |
|---|---|---|---|
| HMSH2/MutS | | HNPCC | Mismatch repair; MutS Homologue |
| HPMS1 | | HNPCC | Mismatch repair; MutL Homologue |
| hPMS2 | | HNPCC | Mismatch repair; MutL Homologue |
| INK4/MTS1 | Adjacent INK-4B at 9p21; CDK complexes | Candidate MTS1 suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T antigen | Mutated >50% human tumors, including hereditary Li-Fraumeni syndrome | Transcription factor; checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; osteosarcoma; breast cancer; other sporadic cancers | Interact cyclin/cdk; regulate E2F transcription factor |
| XPA | | xeroderma pigmentosum; skin cancer predisposition | Excision repair; photo-product recognition; zinc finger |

VI. Therapeutic Uses: Formulations and Routes of Administration

ErbB-2 is overexpressed in a number of cancer types including those involving the female genital tract (e.g., endometrial cancer), gastric cancer and prostate cancer. A preliminary clinical study using a variant of Herceptin™ showed some improvement in patients with prostate and kidney cancer. However, a primary target for ErbB-2 targeted therapies is breast cancer, of which 20-30% show overexpression of this marker. Thus, in accordance with the present invention, there are provided therapeutic methods designed to intervene in such ErbB-2 related cancers. These therapies may facilitate tumor growth inhibition, reduction in tumor size, induction of apoptosis in tumor cells, inhibition or reduction in metastasis formation, or otherwise result in an improvement in the clinical situation of a cancer patient, including improving one or more symptoms of cancer.

Trastuzumab is commercially available as HERCEPTIN from Genentech, which provides it in a vial as a sterile, white to pale yellow, preservative-free lyophilized powder for intravenous (IV) administration. Each vial has 440 mg Trastuzumab, 9.9 mg L-histidine HCl, 6.4 mg L-histidine, 400 mg trehalose dihydrate, and 1.8 mg polysorbate 20, USP, which is a pharmaceutically acceptable formulation.

The number of mg of Herceptin needed can be determined based on a loading dose of 4 mg/kg body weight, or a maintenance dose of 2 mg/kg body weight. The weekly maintenance dose can be continued until disease progression. For outpatient administration, patients are given a 4-mg/kg loading dose as an infusion over 90 minutes. A 2-mg/kg weekly maintenance dose can be administered as a 30-minute infusion if the prior dose was well tolerated.

The phrases "pharmaceutically or pharmacologically acceptable" refer to molecular entities and compositions that do not produce an adverse, allergic or other untoward reaction when administered to a human. As used herein, "pharmaceutically acceptable carrier" includes any and all solvents, dispersion media, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The compositions will be sterile, be fluid to the extent that easy syringability exists, stable under the conditions of manufacture and storage.

For non-Herceptin ErbB2 targeting agents, the actual dosage amount of a composition of the present invention administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

Although it is most preferred that compositions of the present invention be prepared in sterile water containing other non-active ingredients, made suitable for injection, solutions of such active ingredients can also be prepared in water suitably mixed with a surfactant, such as hydroxypropylcellulose, if desired. Dispersions can also be prepared in liquid polyethylene glycols, and mixtures thereof and in oils. The carrier can also be a solvent or dispersion medium containing, for example, water, ethanol, polyol (for example, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Upon formulation, solutions will be administered in a manner compatible with the dosage formulation and in such amount as is therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The compositions of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally using aerosol, injection, infusion, continuous infusion, localized perfusion bathing target cells directly or via a catheter or lavage. In particular, the invention may provide local, regional or systemic administration with respect to the tumor location. Typically, such compositions are prepared as injectables, either as liquid solutions or suspensions; solid forms suitable for preparing solutions or suspensions upon the addition of a liquid prior to injection can also be prepared; and the preparations can also be emulsified.

VII. Kits

Any of the compositions described herein may be comprised in a kit. In a non-limiting example, one or more reagents for evaluating PTEN expression can be provided in a kit, alone or in combination with reagents for evaluating whether a cancer is an ErbB2-overexpressing cancer. The kits may thus comprise, in suitable container means, nucleic acids, antibodies, or other polypeptides that can be used to determine PTEN and/or ErbB2 expression in a sample. Such reagents that can be included in kits of the invention are discussed herein. In some embodiments, the reagents are attached or fixed to a support, such as a plate, chip or other non-reactive substance. For example, a reagent can be fixed to a microtiter well, and the sample placed in the well to determine the expression level of PTEN and/or ErbB2.

The kits may comprise a suitably aliquoted nucleic acids that can be used as probes or primers; alternatively, it may comprise a suitably aliquoted antibody that can be used in immunohistochemical detection methods or any other method discussed herein or known to those of skill in the art.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the containers in close confinement for commercial sale. Such means may include injection or blow-molded plastic containers into which the desired vials are retained.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Experimental Procedures

Antibodies and reagents. PTEN antibodies were from Santa Cruz Biotechnology (A2B1, Santa Cruz, Calif.) and Lab Vision Corp. (Ab-2, Fremont, Calif.), antibodies to Akt, phospho-Akt and Y416-phosphorylated Src were from Cell Signaling Technology (Beverly, Mass.), antibodies to ErbB2 and v-Src (Ab-1) were from Calbiochem (La Jolla, Calif.), antibodies to the 85-kDa subunit of PI3K, phosho-ErbB2 and phosph-tyrosine (4G10) were from Upstate Biotechnology Inc. (Waltham, Mass.); antibody to phospho-tyrosine (PY20) was from BD Biosciences (San Diego, Calif.); and trastuzumab from Genentech Inc. (South San Francisco, Calif.). LY294002 was from Cell Signaling Technology, Wortmannin, PP2, and AG1879 were from Calbiochem; Enolase was from Sigma (St. Louis, Mo.); and Taxol was from Bristol Myers-Squibb (Princeton, N.J.). Src/CA mutant expression vector was provided by Dr. David Shalloway (Cornell University).

Cell culture. SKBr3 cells were from the American Type Culture Collection (Manassas, Va.) and maintained in McCoy's 5A containing 15% fetal bovine serum (FBS), BT474 sub-line was maintained in DMEM/F12 with 10% FBS. Both lines have the wild-type PTEN gene (Li et al., 1997).

PI3K Activity assay. PI3K activities were determined in the PY20 antibody immunoprecipitates of untreated or trastuzumab-treated lysates as done previously (Tan et al., 1999).

Src kinase assay. Equal amounts of cell lysates were immunoprecipitated with anti-Src antibody (0P07, Oncogene Tesearch Products, Boston, Mass.). The precipitates were washed and incubated with 250 µg/ml enolase, 2 µCi of [$\gamma^{32}$P]ATP, and 3 µl of 100 mM ATP in 40 µl of kinase buffer. After 30 min at 37° C., the samples were boiled in 15 µl of 6×SDS sample buffer for 5 min and then subjected to SDS-PAGE. The $^{32}$P-labeled enolase was visualized by autoradiography.

Figure 2A:
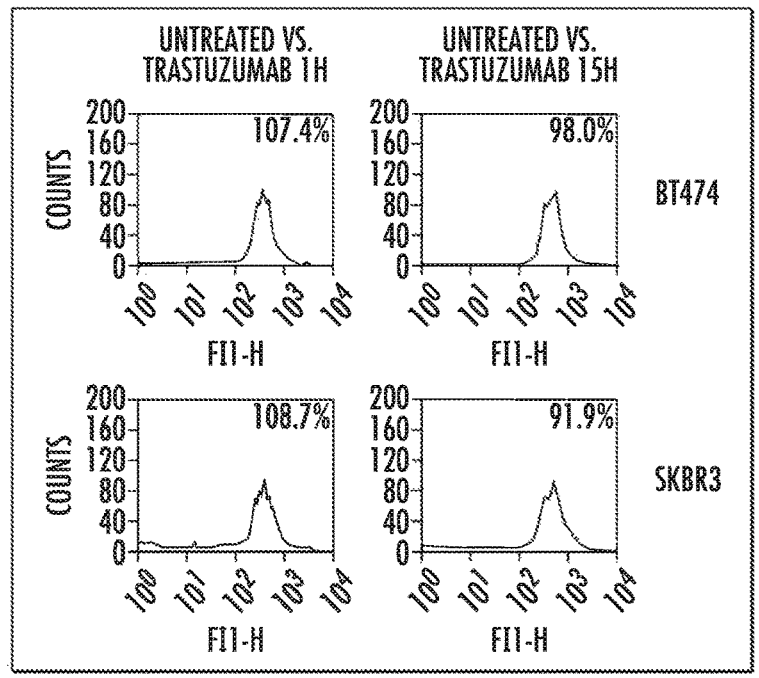
FIGS. 2A-2B. ErbB2 remains localized on the cell membrane up to 15 h of trastuzumab treatment.

Antisense Delivery in vitro. Antisense oligonucleotides against PTEN (ISIS116847: 5'-CTGCTAGCCTCTG-GATTTGA-3') (SEQ ID NO:3) and control oligonucleotides (ISIS 116848: 5'-CTTCTGGCATCCGGTTTAGA-3' (SEQ ID NO:4), with six base mismatches to ISIS 116847) have been described (Butler et al., 2002). Cells were plated in 100-mm dishes at 30% confluence and transfected with oligonucleotides (12.5 nM for BT474 and 25 nM for SKBr3 cells) twice using Oligofectamine (Life Technologies, Rockville, Md.) 24 and 72 h post-plating. Ninety-six hours post-plating, cells were re-plated for individual assays described in this report. PTEN expression was determined 120 h post-plating (FIG. 2A).

Cell viability assay. Cells were seeded at $1-5 \times 10^3$ cells/well in 96-well plates after oligonucleotide transfection. Viable cells were determined by CellTiter 96 AQueous Non-Radioactive Cell Proliferation Assay (Promega, Madison, Wis.).

Preparation of Cell Lysates, Immunoprecipitation, and Western Blot Analysis. Cells at 70%-80% confluence were treated with each reagent indicated in the individual experiments. For PTEN phosphotyrosine immunoblots, ErbB2 IP, and Src IP, cells were treated with 30 mM pervanadate for 10 min as described (Lu et al., 2003). Unless noted, cells were washed with PBS and lysed in IP buffer with protease inhibitor cocktail (Sigma Chemical Co., St. Louis, Mo.). Immunoprecipitation and Western blot analysis were performed (Yu et al., 1998).

PTEN phosphatase assay. PTEN phosphatase activity was measured as described with minor modifications (Georgescu et al., 1999). Each assay was performed in 50 µl buffer containing 100 mM Tris-HCl (pH 8.0), 10 mM DTT, and 100 µM water-soluble diC8-$PIP_3$ (Echelon, Salt Lake City, Utah). Reactions contained PTEN immunoprecipitated from cell lysates on protein G-agarose beads. Prior to immunoprecipitation with PTEN antibody (Ab-2), lysates were precleared with protein G-agarose beads to eliminate trastuzumab used for treatment. After immunoprecipitation, the beads were washed once in lysis buffer; five times in low-stringency buffer containing 20 mM Hepes (pH 7.7), 50 mM NaCl, 0.1 mM EDTA, and 2.5 mM $MgCl_2$; and once in phosphatase assay buffer lacking $PIP_3$. Reactions were incubated for 40 min at 37° C. and transferred to a 96-well plate. Release of phosphate from substrate was measured using Biomol Green Reagent (Biomol Research Laboratories, Inc., Plymouth Meeting, Pa.).

Separation of membrane-bound and cytosolic proteins. Cells were lysed in saponin buffer (0.01% saponin, 10 mM Tris-HCL at pH 7.4, 140 mM NaCl, 5 mM EDTA, 2 mM EGTA, 0.2 mM sodium vanadate, 50 mM NaF, 25 mM β-glycerophosphate) containing protease inhibitor cocktail (Sigma). Proteins were extracted for 20 min on ice, and samples centrifuged at 14,000 g for 30 min at 4° C. The saponin soluble pool (cytosolic pool) was collected (Palka and Green, 1997). The remaining pellet was rinsed with saponin buffer once, extracted in IP buffer, and centrifuged to remove insoluble materials. The supernatant was collected (membrane-bound pool).

Analysis of internalization using flow cytometry. Immunofluorescent flow cytometry was performed as described (Drebin et al., 1985; van Leeuwen et al., 1990) using anti-ErbB2 (Ab5, Calbiochem) as the primary antibody.

BrdU incorporation assay. S-phase cells were detected using 5-bromo-2'-deoxyuridine (BrdUrd) Labeling and Detection Kit I (Roche Molecular Biochemicals, Indianapolis, Ind.).

Immunofluorescence staining. It was performed as described in (Tan et al., 2002).

Animal experiment. Female athymic nude mice (Harlan Sprague Dawley, Indianapolis, Ind.) were implanted with 0.72-mg 60-day-release 17β-estradiol pellets (Innovative Research, Sarasota, Fla.) and irradiated at 3.5 Gy prior to inoculation. BT474 cells ($8 \times 10^6$) in 200 µl of PBS and Matrigel (BD Biosciences, Bedford, Mass.) mixture (1:1 ratio) were injected subcutaneously into a mouse mammary fat pad (mfp). When the mfp tumor volume reached >150 $mm^3$, the tumor was treated with PTEN antisense or control mismatched oligonucleotides (30 µg/week) in saline. One week later, mice received trastuzumab (10 mg/kg) or vehicle (PBS) twice/week, combined with LY294002 (100 mg/kg) or vehicle (DMSO) three times/week. Tumor diameters were serially measured with calipers and tumor volumes calculated: volume=$width^2 \times length/2$. Each treatment group contained 8-12 mice. Unpaired Student's t-test was used to assess statistical significance.

Patient samples. Forty-seven ErbB2-overexpressing primary breast carcinomas were collected from patients who subsequently developed metastatic breast cancer and received trastuzumab plus taxane chemotherapy (paclitaxel or docetaxel) (Esteva et al., 2002; Seidman et al., 2001). Primary breast carcinomas not selected for ErbB2-overexpressing tumors from 37 patients who subsequently developed metastatic breast cancer and received taxane without trastuzumab were collected as controls (Holmes et al., 1991; Valero et al., 1995). The 47 patients were treated between 1998-2001 and the 37 patients were treated between 1990 and 1991 under IRB-approved clinical trials at The University of Texas M.D. Anderson Cancer Center. Association between clinical response to therapy and PTEN status was tested using chi-square and Fisher's tests.

PTEN Immunohistochemistry. Slides of formalin-fixed, paraffin-embedded tissue sections (4 µm) were incubated with primary antibody (1:500) against PTEN (Podsypanina et al. 2001) (Ab-2, Lab Vision Corp.). Immunodetection was performed with LSAB2 kit (DAKO, Carpinteria, Calif.), color development with 3-3'-diaminobenzidine, and counterstaining with hematoxylin. PTEN expression level was scored semiquantitatively based on staining intensity and distribution using the immunoreactive score (IRS) as described (Chui et al., 1996; Fredrichs et al., 1993) and as following: IRS=SI (staining intensity)×PP (percentage of positive cells). SI was determined as 0=negative; 1=weak; 2=moderate; and 3=strong. PP was defined as 0, <1%; 1, 1%-10%; 2, 11%-50%; 3, 51%-80%; and 4, >80% positive cells. Ten visual fields from different areas of each tumor were used for the IRS evaluation. Negative control slides without primary antibody were included for each staining. Normal breast epithelium or vascular endothelium knoen to express normal PTEN was used as positive controls.

ErbB2 status. ErbB2 gene amplification in patients' samples was determined by fluorescence in situ hybridization (FISH) using PathVysion FISH assay (Vysis, Inc., Downers Grove, Ill.). ErbB2 protein overexpression was determined by IHC as previously described (Jacobs et al., 1999).

Example 2

Trastuzumab Activates PTEN in Breast Cancer Cells

Figure 1B:
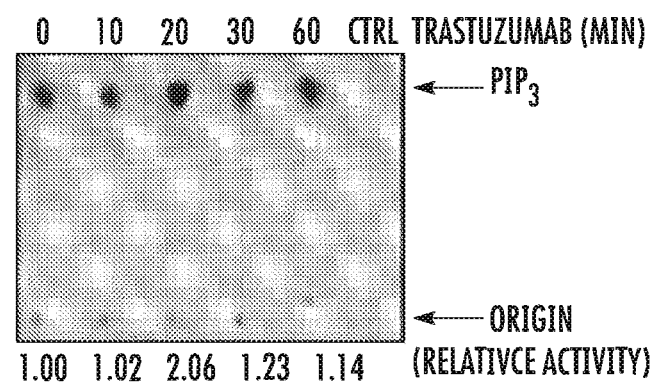
Figure 1C:
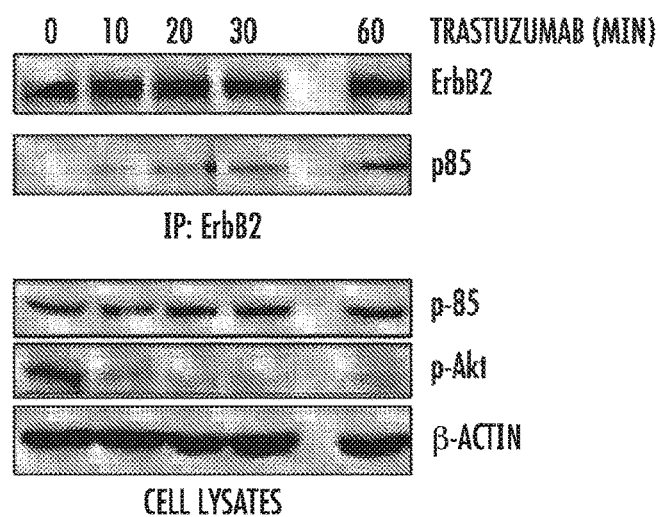
Figure 2B:
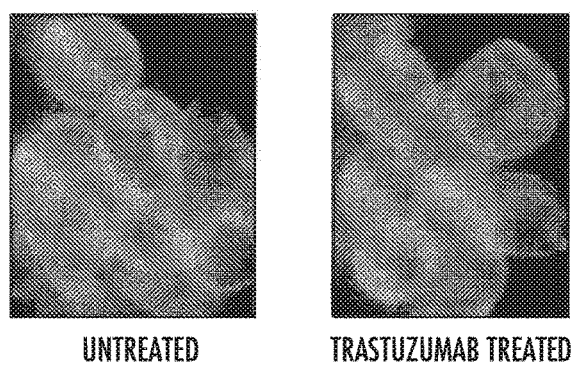

In our initial investigation of the mechanisms of trastuzumab's anti-tumor function, the inventors observed that >20 h trastuzumab treatment of BT474 and SKBr3 human breast cancer cell lines overexpressing endogenous ErbB2 led to ErbB2 downregulation, dephosphorylation, and receptor internalization as expected (Lee et al., 2002). However, 1 h trastuzumab treatment (2-10 µg/ml) did not induce ErbB2 downregulation, dephosphorylation, and receptor internalization (FIGS. 1A and 2A and 2B). Surprisingly, 1 h trastuzumab treatment quickly reduced the level of phosphorylated and activated Akt in BT474 and SKBr3 cells when the Akt protein level remained unchanged (FIG. 1A). It is known that Akt is constitutively activated in ErbB2-overexpressing cancer cells and its inhibition is critical for trastuzumab's anti-tumor effect (Ignatoski et al., 2000; Yakes et al., 2002; Zhou et al., 2000). Thus, mechanisms of the rapid Akt dephosphorylation by trastuzumab before ErbB2 downregulation, dephosphorylation, and internalization were investigated. It was determined whether trastuzumab induced rapid Akt dephosphorylation by inhibition of PI3K activation which is the major upstream signaling event leading to Akt phosphorylation (Cantley, 2002). PI3K activity was not inhibited within 1 h of trastuzumab treatment (FIG. 1B). Contrarily, the p85 subunit of PI3K had a transiently increased association with the ErbB2 complex (FIG. 1C), which paralleled a moderate increase of ErbB2 tyrosine phosphorylation by short0time trastuzumab treatment (FIG. 1A). The apparently paradoxical results indicated that the rapid Akt dephosphorylation by 1 h trastuzumab treatment was not due to PI3K inhibition, nor by ErbB2 degradation, dephosphorylation, and internalization, but by some other mechanisms.

Figure 1D:
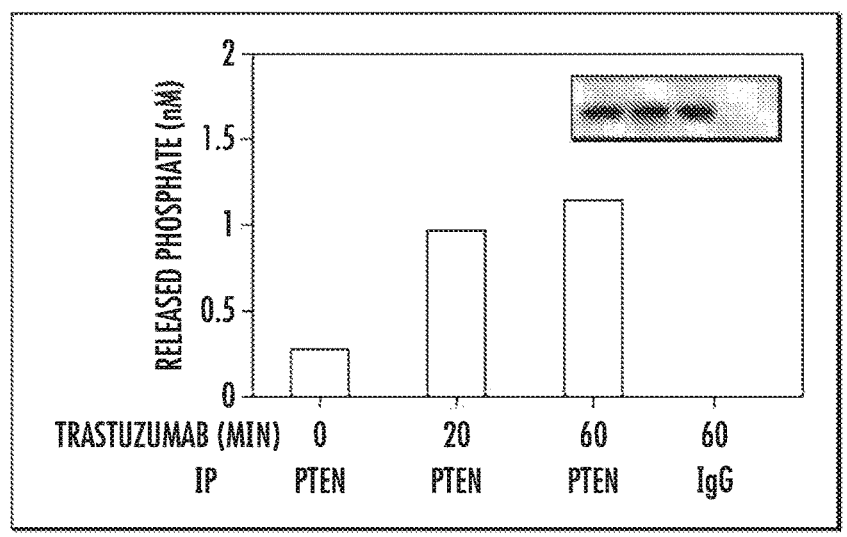

The tumor suppressor PTEN is a dual-phosphatase that negatively regulates Akt activity (Cantley and Neel, 1999; Di Cristofano and Pandolfi, 2000; Leslie and Downes, 2002). Thus, it was determined whether PTEN may be involved in the trastuzumab-mediated rapid Akt dephosphorylation before PI3K inhibition. The phosphatase activity of PTEN was examined in untreated and trastuzumab-treated (20 min or 60 min) SKBr3 cells after immunoprecipitation of a similar amount of PTEN (FIG. 1D, insert). Compared with untreated cells, PTEN activity dramatically increased in cells after 20 min trastuzumab treatment, which continued to increase 60 min after treatment (FIG. 1D). Therefore, trastuzumab treatment indeed led to a rapid increase of PTEN phosphatase activity that could account for the rapid Akt dephosphorylation before PI3K is inhibited by trastuzumab.

Figure 1E:
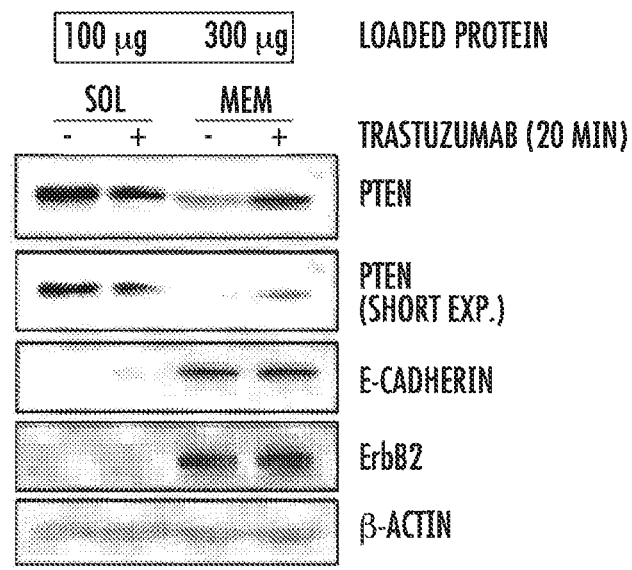

Membrane-associated PTEN is known to be biologically active in cells (corner and Parent, 2002; Iijima and Devreotes, 2002; Wu et al., 2000). To investigate if PTEN activation by trastuzumab is due to recruitment of PTEN to its biologically active sub-cellular location, it was examined whether membrane localization of PTEN is increased by trastuzumab treatment. After treating BT474 cells with or without trastuzumab for 20 min, membrane-bound proteins were separated from cytosolic proteins in cell lysates and PTEN proteins examined by Western blotting (FIG. 1E). In the untreated cells, the majority of PTEN protein was in the cytosolic pool of the lysates, while a very low level of PTEN was detected in the membrane-bound pool. However, upon trastuzumab treatment, PTEN protein in the membrane-bound pool was noticeably enriched. Similar results were also observed in SKBr3 cells (data not shown). This suggested that trastuzumab treatment facilitates PTEN localization to the cell membrane, where this phosphatase is active and functions to dephosphorylate $PIP_3$ to $PIP_2$, leading to Akt dephosphorylation (Cantley and Neel, 1999). Taken together, activation of PTEN is an early molecular event after trastuzumab treatment.

Figure 1F:
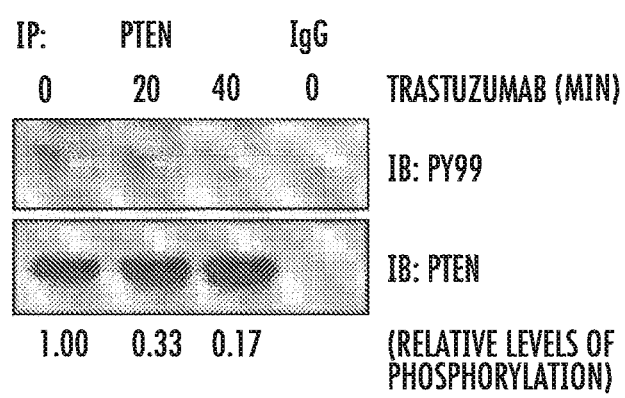

PTEN binds to the cellular membrane through its C2 domain and there are two tyrosine phosphorylation sites in the C2 domain of PTEN (Y240 and Y315) important for PTEN phophatase activity and tumor inhibition function (Koul et al., 2002). Tyrosine phosphorylation of PTEN reduces the capacity of the PTEN C2 domain to bind to the cellular membrane (Lu et al., 2003). Since increased membrane localization of PTEN by trastuzumab treatment in ErbB2-overexpressing cells was observed, the inventors investigated whether this may result from reduced PTEN tyrosine phosphorylation. PTEN was immunoprecipitated from untreated or trastuzumab treated BT474 cells with the A2B1 PTEN antibody and immunoblotted with the PY99 phosphotyrosine antibody (FIG. 1F). Consistent with the notion that PTEN is functionally inactive in ErbB2-overexpressing cells (Lu et al., 1999), the inventors found that PTEN is highly phosphorylated on tyrosine in untreated BT474 cells. However, trastuzumab treatment rapidly reduced PTEN tyrosine phosphorylation in BT474 cells (FIG. 1F), which paralleled the increased PTEN membrane localization and PTEN activation by trastuzumab in these cells (FIGS. 1D and 1E). Thus, trastuzumab induces PTEN activation by increasing the translocation of PTEN from the cytoplasm to the membreane through reducing the inhibitory tyrosine phosphorylation of PTEN. Notably, these events occur before ErbB2 is downregulated and PI3K is inhibited. Therefore, activation of PTEN is an early molecular event after trastuzumab treatment independent of ErbB2 downregulation and PI3K inhibition.

Example 3

PTEN Activation Contributes to Trastuzumab's Anti-proliferation Function

Figure 3A:
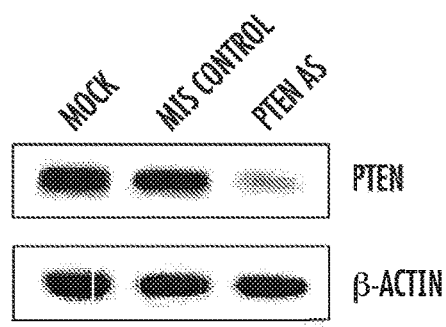
FIGS. 3A-3G. PTEN reduction by PTEN AS oligonucleotides confers resistance to trastuzumab's antiproliferative effects in vitro and in vivo
Figure 3B:
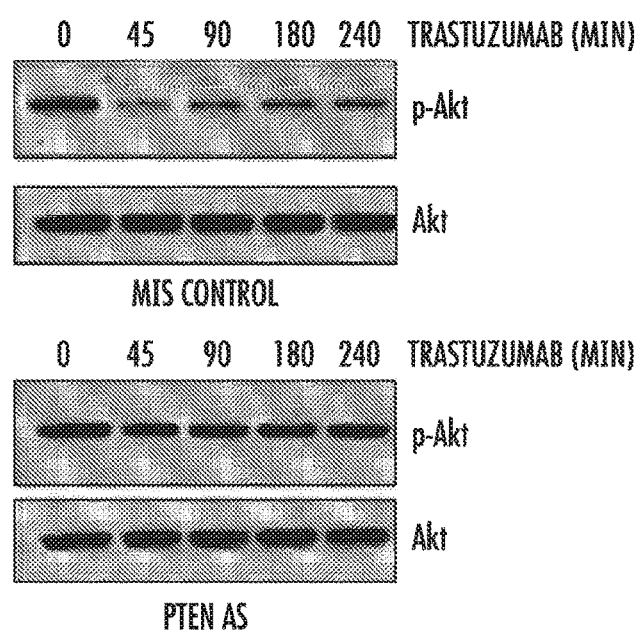

To determine if PTEN activation indeed caused Akt dephosphorylation in response to trastuzumab treatment, SKBr3 breast cancer cells were transfected with PTEN antisense (AS) oligonucleotides (Butler et al., 2002), which inhibited endogenous PTEN expression compared with mock-transfected cells or cells transfected with control mismatched (MIS) oligonucleotides (FIG. 3A). Compared with MIS control-treated cells showing rapid Akt dephosphorylation by trastuzumab treatment (FIG. 3B, top), Akt dephosphorylation was attenuated in PTEN AS-treated cells (FIG. 3B, bottom). This data indicated that PTEN expression is required for the rapid Akt dephosphorylation by trastuzumab.

Figure 3C:
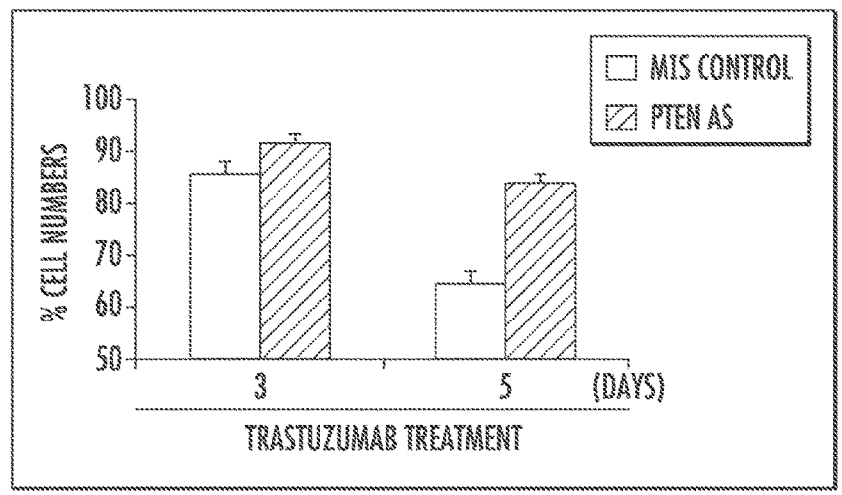
Figure 3D:
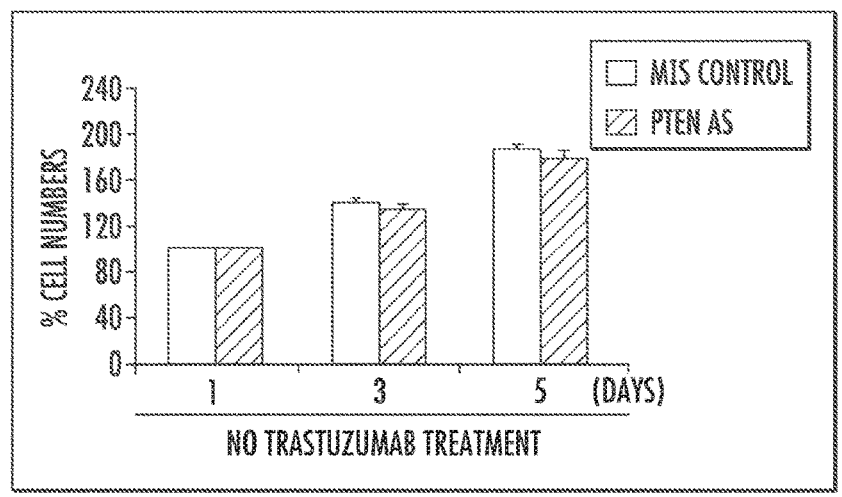
Figure 4A:
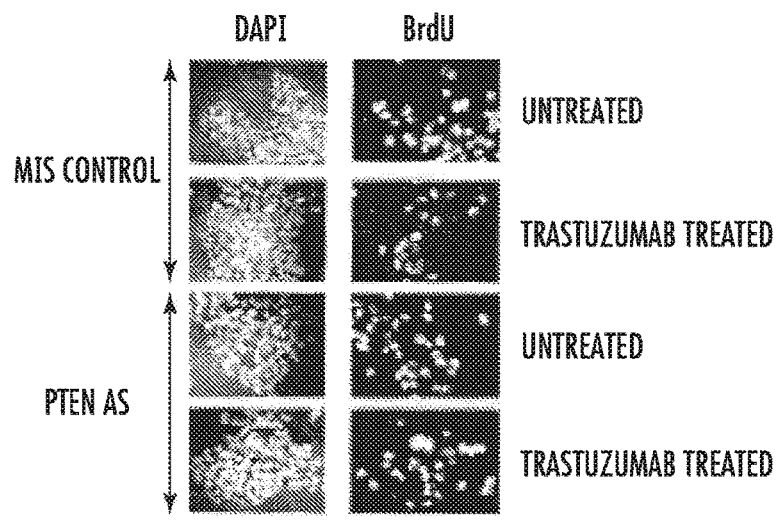
FIGS. 4A-4B. Trastuzumab reduces BrdU incorporation of PTEN normal expressing (MIS) but not of PTEN-deficient (PTEN AS) BT474 cells.
Figure 4B:
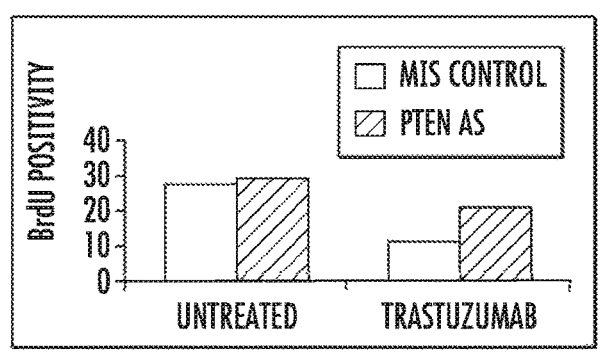

It was investigated whether PTEN activation contributes to the anti-proliferation function of trastuzumab in MIS control and PTEN AS-transfected SKBr3 cells. Inhibition of cell proliferation by trastuzumab was found to be significantly less effective in PTEN AS-treated cells with reduced PTEN than in MIS control-transfected SKBr3 cells having normal PTEN expression (FIG. 3C). Similar results in BT474 cells were observed (FIGS. 4A-4B). This data demonstrated that normal PTEN expression levels are required for the anti-proliferation function of trastuzumab. Without trastuzumab treatment, PTEN reduction by PTEN AS alone had no significant effect on cell proliferation (FIG. 3D), which was consistent with the similar Akt phosphorylation levels in cells treated with PTEN AS alone to that treated with MIS control (FIG. 3B, time 0). That blocking PTEN by PTEN AS only reduced trastuzumab's anti-proliferative function but had no effect on cells without trastuzumab treatment reiterated that PTEN activity is important for trastuzumab function, which reconciles well with the earlier finding that PTEN is activated by trastuzumab (FIGS. 1C and 1D). Thus, PTEN reduction led to resistance to the anti-proliferation effect of trastuzumab in these cells.

Figure 3E:
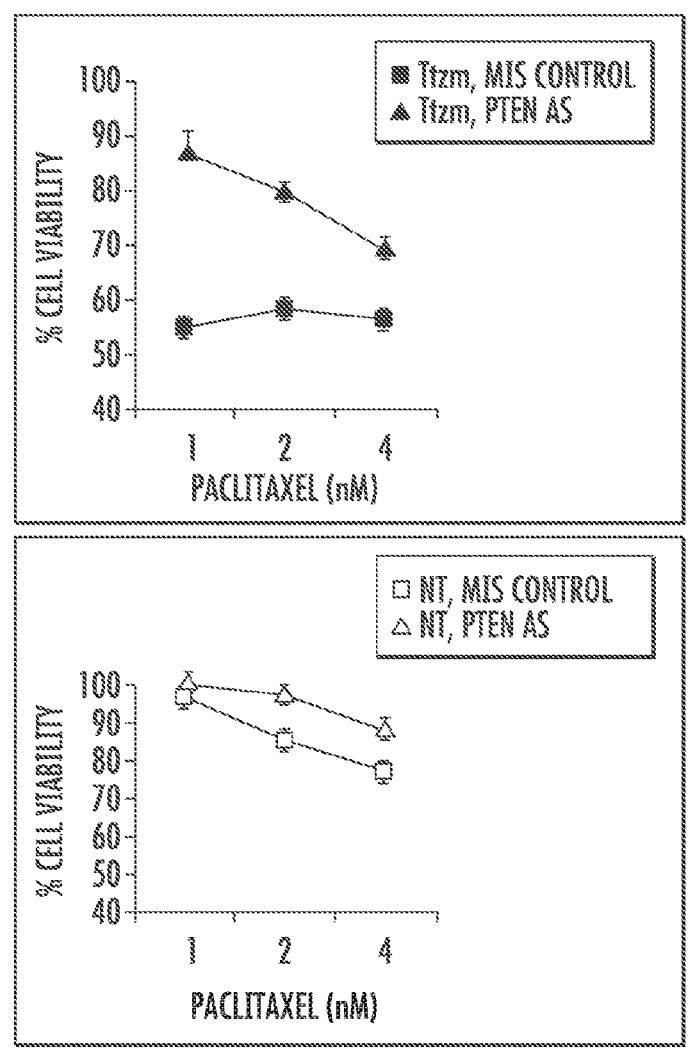

Trastuzumab is mostly used in combination with other chemotherapeutics in the clinic (Slamon et al., 2001). Therefore, it was investigated whether PTEN reduction may confer breast cancer cell resistance to trastuzumab plus paclitaxel chemotherapy. BT474 cells were transfected with PTEN AS or MIS control oligonucleotides, then treated them with or without trastuzumab (2 µg/ml) plus paclitaxel (1 nm), and cell viability was measured 3 days later. MIS control-treated cells with normal PTEN expression showed significant growth inhibition by trastuzumab plus paclitaxel (P<0.0001), whereas PTEN AS-transfected cells were not significantly inhibited (FIG. 3E). Similar results were observed at higher concentrations (2 and 4 nm) of paclitaxel. However, paclitaxel treatment alone without trastuzumab showed no statistically significant difference in cell viability between PTEN AS-transfected and MIS control-transfected cells (FIG. 3E), indicating that PTEN status does not significantly impact breast cancer cell sensitivity to paclitaxel but specifically impacts trastuzumab sensitivity. Together, these results indicated that breast cancer cells with reduced PTEN are resistant to growth inhibition by trastuzumab as a single agent (FIG. 3C) as well as in combination therapy with paclitaxel (FIG. 3E).

Example 4

PTEN Deficiency Contributes to Trastuzumab Resistance In Vivo

Figure 3F:
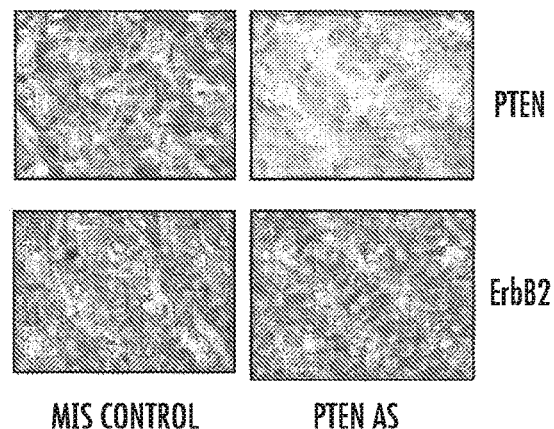
Figure 3G:
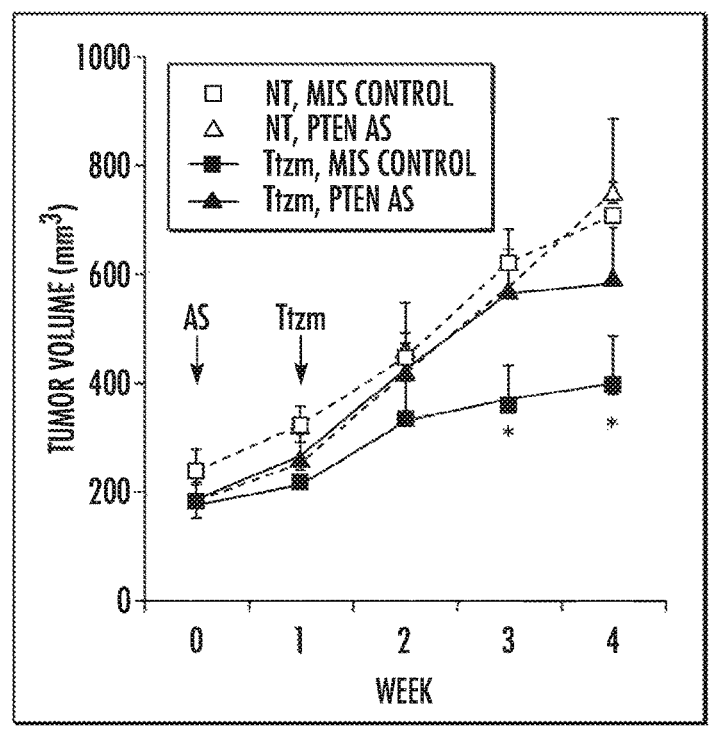

To investigate if reduced PTEN expression may confer breast cancer cell resistance to trastuzumab treatment in vivo, a tumorigenic subline of BT474 human breast cancer cells was injected into the mammary fat pad (mfp) of athymic nude mice. When tumor xenografts reached >150 mm$^3$, PTEN AS or MIS oligonucleotides were injected into the tumor xenografts. One week later, mice were treated with trastuzumab (10 mg/kg) or vehicle twice per week. PTEN expression in tumor xenografts was effectively inhibited by PTEN AS when ErbB2 expression remained the same (FIG. 3F). Trastuzumab treatment only inhibited MIS control-treated tumors expressing normal PTEN, but not PTEN AS-treated tumors with reduced PTEN (FIG. 3G). Without trastuzumab treatment, PTEN AS and MIS treated tumors had similar tumor growth rates (FIG. 3G). These results demonstrated that PTEN reduction confers breast tumor xenografts resistance to the anti-tumor function of trastuzumab in vivo.

Example 5

PI3K Inhibitors Rescue PTEN Loss-induced Trastuzumab Resistance

Figure 5A:
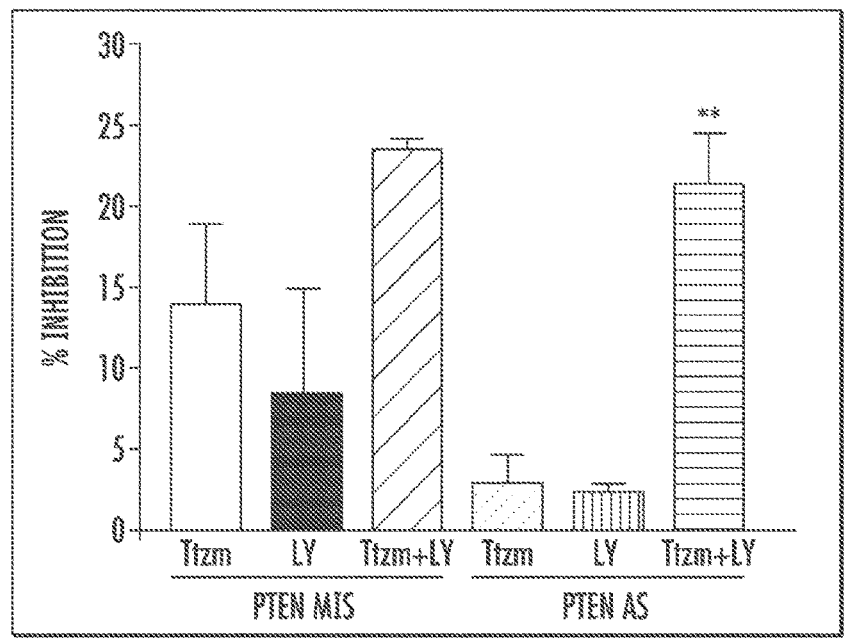
FIGS. 5A-5C. PI3K inhibitors enhance trastuzumab's antiproliferation function in PTEN-reduced BT474 cells in vitro and in vivo
Figure 5B:
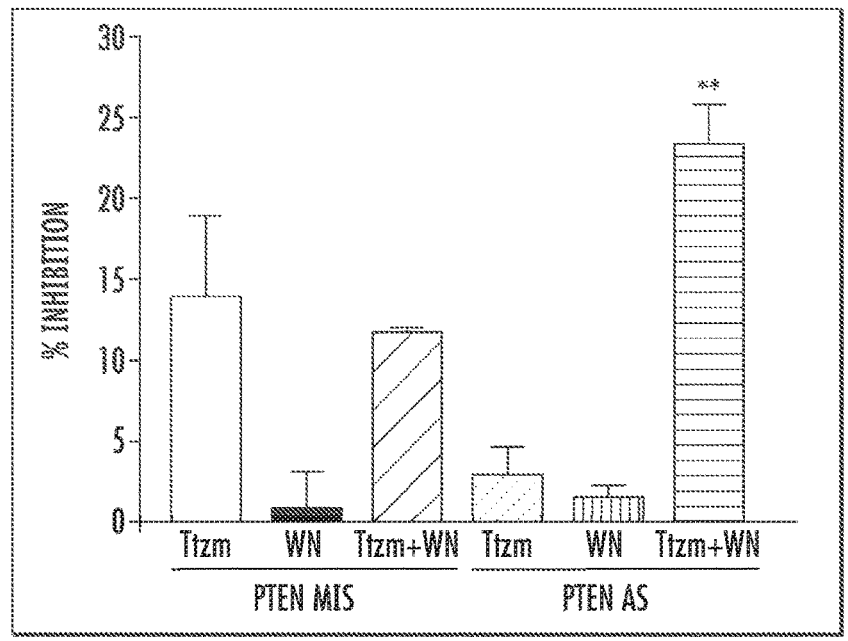
Figure 5C:
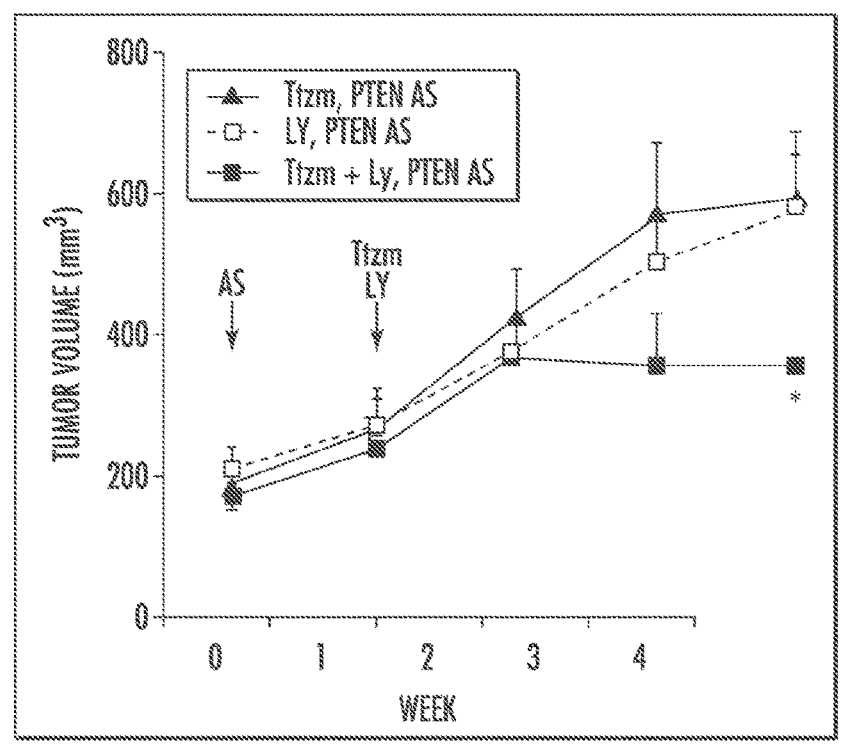

The above data clearly demonstrate that PTEN deficiency confers trastuzumab resistance in breast cancer. In search of strategies for overcoming trastuzumab resistance from the loss of PTEN, it was reasoned that since PI3K antagonizes PTEN function, inactivation of PI3K may rescue trastuzumab resistance from PTEN deficiency. The inventors investigated whether PI3K inhibitors that are known to quickly induce Akt dephosphorylation in ErbB2-overexpressing cells may reverse trastuzumab resistance in PTEN-deficient breast cancer cells (Xiong et al., 2001). BT474 cells were transfected with MIS and PTEN AS oligonucleotides, then treated them with trastuzumab, the PI3K inhibitor LY294002, or trastuzumab plus LY294002. The inventors then determined cell viability 3 days later (FIG. 5A). The MIS-treated cells are more sensitive to trastuzumab-mediated growth inhibition than the PTEN AS-treated cells, and the combination treatment inhibited the viability of MIS-treated cells slightly better than trastuzumab alone or LY294002 alone (p>0.05). However, the LY294002 plus trastuzumab combination inhibited cell viability significantly better than trastuzumab alone or LY294002 alone in PTEN AS-treated cells (p<0.01). Similarly, another PI3K inhibitor, Wortmannin, in combination with trastuzumab, also inhibited PTEN AS-treated BT474 cells significantly better than either treatment alone (p<0.01), whereas the combination had a similar inhibitory effect as trastuzumab alone in MIS-treated cells (FIG. 5B). In vivo, trastuzumab combined with the PI3K inhibitor LY294002 was also significantly (p<0.05) more effective than trastuzumab alone or LY294002 alone in inhibiting PTEN AS-treated BT474 tumor xenografts in mice (FIG. 4C). These results indicate that PI3K inhibitors could overcome trastuzumab resistance in PTEN-deficient breast cancer cells.

Example 6

Figure 6A:
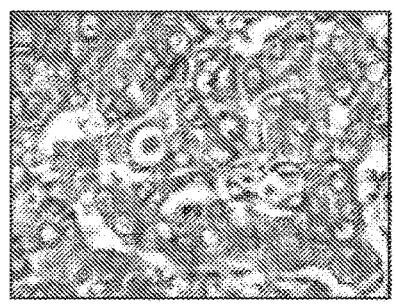
Figure 6A:
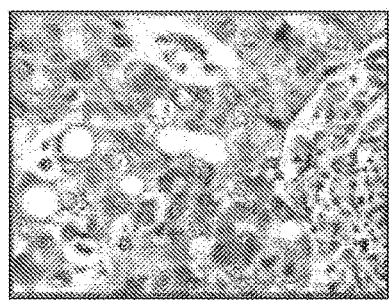
Figure 6A:
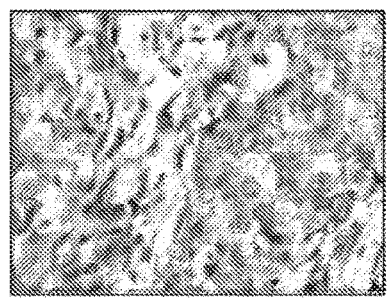
Figure 6A:
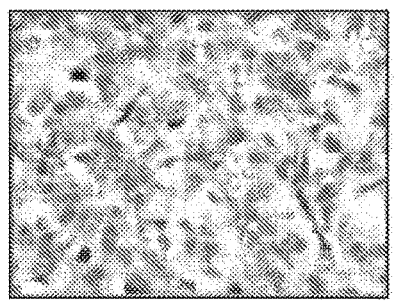
Figure 7:
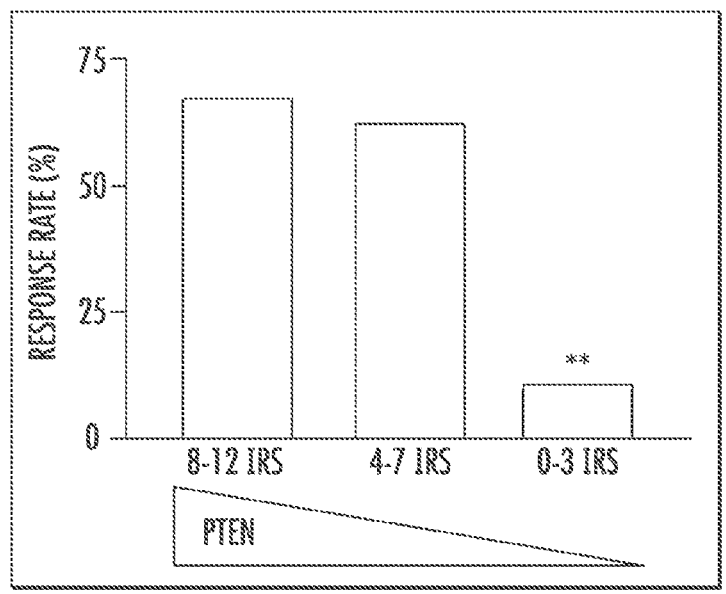
FIG. 7. The response rate to trastuzumab decreases as PTEN expression (IRS score) decreases. The clinical response rate to trastuzumab includes either complete response or partial response in patients with breast cancers expressing three ranges of PTEN IRS of 0-3, 4-7, and 8-12. The Cochran-Armitage test was performed on the data which supports the trend hypothesis that the probability of response to trastuzumab decreases as PTEN IRS decreases. ** P<0.01
Figure 8:
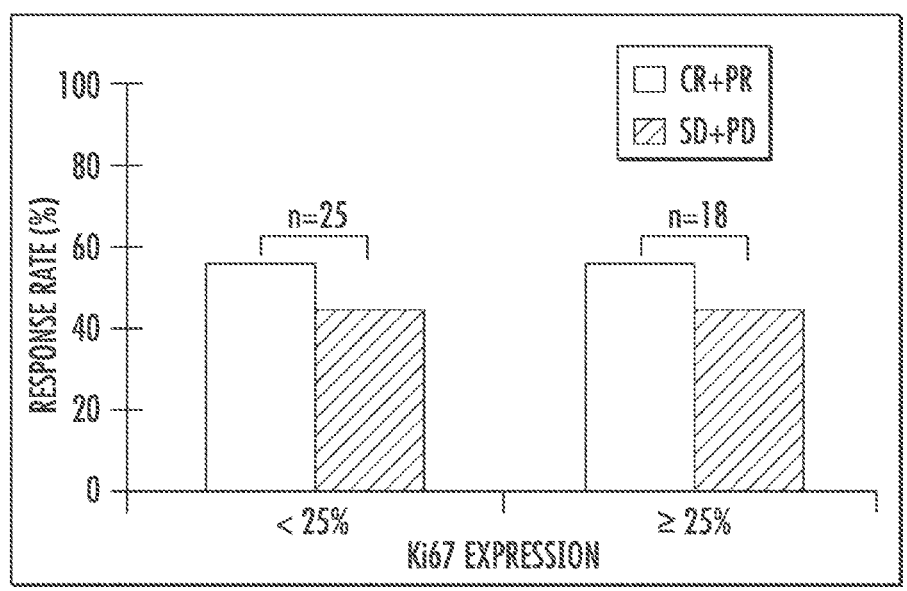
FIG. 8. Ki67 expression levels do not correlate with clinical response to trastuzumab plus taxane treatment. Ki67 high expression was defined as $\geq$ 25% Ki67 positive cells. Ki67 staining was performed in 43 samples due to limited sample availability. CR, complete response; PR, partial response; SD, stable disease; PD, progressive disease

Patients with PTEN-deficient Breast Cancers Have a Poor Clinical Response to Trastuzumab To explore the clinical significance of PTEN deficiency in predicting a poor response to trastuzumab-based therapy in patients, PTEN expression was evaluated in 47 ErbB2-overexpressing primary breast carcinomas from patients who subsequently developed metastatic breast cancer and received trastuzumab plus taxane chemotherapy (paclitaxel or docetaxel) (Esteva et al., 2002; Seidman et al., 2001). As controls, PTEN expression was evaluated in primary breast carcinomas not selected for ErbB2 overexpression from 37 patients who subsequently developed metastatic breast cancer and received taxane without trastuzumab (Holmes et al., 1991; Valero et al., 1995). Immunohistochemical staining using anti-PTEN antibodies revealed that PTEN expression in these tumors was heterogeneous with different intensities. Thus, PTEN expression levels were semi-quantified using immunoreactive scores (IRS) calculated by multiplying the percentage of PTEN positive cells (scored 0 to 4) with the PTEN staining intensity (1 to 3) (Joki et al., 2000). IRS of 0 to 12 represents PTEN staining from a non-detectable level in PTEN-lost tumors to positive full expression seen in normal (non-cancerous) individuals (FIG. 6A). A loss of PTEN (IRS<9) was observed in 36.2% of the tumor samples examined (17/47), which is consistent with previous reports on loss of PTEN expression in approximately 40% breast cancers using IHC staining (Depowski et al., 2001; Perren et al., 1999). Remarkably, breast cancer patients with PTEN low or negative tumors (IRS 6-0) had significantly lower complete and partial response (CR+PR) rates to trastuzumab plus taxane therapy than patients with PTEN positive tumors (35.7% vs. 66.7%, P<0.05) (FIG. 6B, left). Using more stringent criteria for loss of PTEN (IRS<4), patients with PTEN negative tumors demonstrated a striking, highly significant (P<0.01) worse response to trastuzumab plus taxane therapy than patients with PTEN positive tumors (11.1% versus 65.8% CR+PR) (FIG. 6B, right). Furthermore, a statistically significant trend was identified, suggesting that the probability of response to trastuzumab decreases as PTEN IRS decreases (P<0.01) (FIG. 7). However, among the 37 patients treated by taxane without trastuzumab, patients with PTEN-deficient tumors had similar response (CR+PR) rates to those with PTEN-positive tumors (p=0.04 when PTEN loss is defined as IRS 0-6; p=0.74 when PTEN loss is defined as IRS<4. These data clearly demonstrate that PTEN loss does not confer breast cancer resistance to taxane but to trastuzmab. To confirm that PTEN is a specific marker for trastuzumab responsiveness, Ki67, a known prognostic marker for breast cancers, was examined (Faneyte et al., 2003), which may also predict trastuzumab responsiveness. Ki67 did not correlate with clinical response to trastuzumab plus taxane treatment in this group (FIG. 8). Interestingly, although patients with ErbB2 FISH positive and/or IHC 3+ ErbB2 overexpression breast cancers seemed to respond to trastuzumab plus taxane better than patients with ErbB2 FISH negative and/or 2+ ErbB2 overexpression cancer (59% vs. 37%), the difference was not statistically significant (FIG. 6C). However, among patients with ErbB2 FISH positive and/or IHC 3+ ErbB2 overexpressing breast cancers, PTEN low or negative tumors (IRS 3-0) had significantly lower response (CR+PR) rates than patients with PTEN positive tumors (12.5% vs. 71%, P<0.01) (FIG. 4D).

Example 7

Trastuzumab Activates PTEN by Inhibiting Src Association with ErbB2

To investigate how trastuzumab inhibits PTEN tyrosine phosphorylation, the inventors examined whether trastuzumab may inhibit Src tyrosine kinase, since Src activation has recently been reported to increase PTEN tyrosine phosphorylation (Lu et al., 2003). Compared to untreated cells, trastuzumab treatment rapidly inhibited Src kinase activity and rapidly reduced Src phosphorylation on Y416, an indicator of Src activity (Frame, 2002). Reduced Src-Y416 phosphorylation corresponded to reduced PTEN tyrosine phosphorylation.

Src is known to bind to ErbB2 and is thus activated in ErbB2-overexpressing cancer cells (Belsches-Jablonski et al., 2001; Muthuswamy and Muller, 1995). To explore the mechanisms of trastuzumab-mediated Src inhibition, the inventors examined whether Src binding to ErbB2 is inhibited by trastuzumab treatment in BT474 cells. Trastuzumab induced a very rapid and dramatic reduction of ErbB2 bound Src, indicating that trastuzumab inhibited Src activity in ErbB2 overexpressing cells most likely by inhibiting Src binding to ErbB2.

To further confirm that Src inhibition can reduce PTEN tyrosine phosphorylation in ErbB2-overexpressing breast cancer cells, the inventors examined whether the Src kinase inhibitor PP2 may reduce PTEN tyrosine phosphoryulation in the ErbB2-overexpressing 435.eB breast cancer cells (Yu et al., 1998b). Compared to the solvent 10% dimethyl sulfoxide (DMSO)-treated 435.eB cells, PP2 treatment effectively inhibited Src phosphorylation on Y416 and also dramatically reduced tyrosine phosphorylation of PTEN, similar to trastuzumab's effect. Contrarily, the eB/SrcCA cells, which are 435.eB cells stably expressing a constitutively activated Src (Chan et al., 2003) and having higher levels of Src-Y416 phosphorylation and Src activity, showed a dramatic increase of PTEN tyrosine phosphorylation compared to the 435.eB cells. Furthermore, although trastuzumab treatment effectively increased the PTEN membrane translocation in the 435.eB cells, PTEN membrane translocation by trastuzumab in the eB/SrcCA cells expressing constitutively activated Src was less effective. Together, the data indicate that trastuzumab treatment inhibits Src binding to ErbB2 in ErbB2-overexpressing breast cancer cells, thus inhibiting Src kinase activity, which leads to reduced PTEN tyrosine phosphorylation and increased PTEN membrane localization and activity.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,683,195
U.S. Pat. No. 4,683,202
U.S. Pat. No. 4,800,159
U.S. Pat. No. 4,883,750
U.S. Pat. No. 4,946,773
U.S. Pat. No. 5,279,721
U.S. Pat. No. 5,739,169
U.S. Pat. No. 5,801,005
U.S. Pat. No. 5,824,311
U.S. Pat. No. 5,830,880
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,846,945
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517

U.S. Pat. No. 5,925,525
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391

Abbondanzo et al., *Am. J. Clin. Pathol.*, 93(5):698-702, 1990.
Albanell and Baselga, *J. Natl. Cancer Inst.*, 93(24):1830-1832, 2001.
Allred et al., *Arch. Surg.*, 125(1):107-113, 1990.
Arap et al., *Cancer Res.*, 55(6):1351-1354, 1995.
Austin-Ward and Villaseca, *Rev. Med. Chil.*, 126(7):838-45, 1998.
Ausubel et al., In: *Current Protocols in Molecular Biology*, John, Wiley & Sons, Inc, New York, 1996.
Bajorin et al., *J. Clin. Oncol.*, 6(5):786-792, 1988.
Bakhshi et al., *Cell*, 41(3):899-906, 1985.
Bange et al., *Nat. Med.*, 7(5):548-552, 2001.
Baselga et al., *J. Clin., Oncol.*, 14(3):737-744, 1996.
Bellus, *J. Macromol. Sci. Pure Appl. Chem.*, A31(1): 1355-1376, 1994.
Belsches-Jablonski et al., *Oncogene*, 20:1465-1475, 2001.
Brown et al. *Immunol. Ser.*, 53:69-82, 1990.
Bukowski et al., *Clin. Cancer Res.*, 4(10):2337-2347, 1998.
Butler et al., *Diabetes*, 51(4):1028-1034, 2002.
Caldas et al., *Nat. Genet.*, 8(1):27-32, 1994.
Cantley and Neel, *Proc. Natl. Acad. Sci. USA*, 96(8):4240-4245, 1999.
Cantley, *Science*, 296(5573):1655-1657, 2002.
Chan et al., *J. Biol. Chem.*, 278:44075-44082, 2003.
Cheng et al., *Cancer Res.*, 54(21):5547-5551, 1994.
Christodoulides et al., *Microbiology*, 144(Pt 11):3027-3037, 1998.
Chui et al., *Br. J. Cancer*, 73:1233-1236., 1996.
Cleary and Sklar, *Proc. Natl. Acad. Sci. USA*, (21):7439-7443, 1985.
Cleary et al., *J. Exp. Med.*, 164(1):315-320, 1986.
Cobleigh et al., *J. Clin., Oncol.*, 17(9):2639-2648, 1999.
Comer and Parent, *Cell*, 109(5):541-544, 2002.
Culver et al., *Science*, 256(5063):1550-1552, 1992.
Davidson et al., *J. Immunother.*, 21(5):389-398, 1998.
De Jager et al., *Semin. Nucl. Med.*, 23(2):165-179, 1993.
Depowski et al., *Mod. Pathol.*, 14(7):672-676, 2001.
Di Cristofano and Pandolfi, *Cell*, 100(4):387-390, 2000.
Dillman, *Cancer Biother. Radiopharm.*, 14(1):5-10, 1999.
Doolittle and Ben-Zeev, *Methods Mol. Biol.*, 109:215-237, 1999.
Drebin et al., *Cell*, 41(3):697-706, 1985.
Esteva et al., *J. Clin., Oncol.*, 20(7):1800-1808, 2002.
European Appln. 320 308
European Appln. 329 822
Faneyte et al., *Br. J. Cancer*, 88(3):406-412, 2003.
Fodor et al., *Biochemistry*, 30(33):8102-8108, 1991.
Frame et al., *Biophys. Acta*, 1602:114-130., 2002.
Fredrichs et al., *Cancer*, 72:3641-3647, 1993.
Frohman, In: *PCR Protocols: A Guide To Methods And Applications*, Academic Press, N.Y., 1994.
GB Appln. 2 202 328

Georgescu et al., *Proc. Natl. Acad. Sci. USA*, 96(18):10182-10187, 1999.
Gulbis and Galand, *Hum. Pathol.*, 24(12):1271-1285, 1993.
Hacia et al., *Nature Genet.*, 14:441-449, 1996.
Hanibuchi et al., *Int. J. Cancer*, 78(4):480-485, 1998.
Harlow and Lane, Antibodies: A Laboratory Manual. Cold Spring Harbor Laboratory Press, Cold Spring harbor, NY, 553-612, 1988.
Hellstrand et al., *Acta Oncol.*, 37(4):347-353, 1998.
Holmes et al., *J. Natl. Cancer Inst.*, 83:1797-1805, 1991.
Hudziak et al., *Mol. Cell Biol.*, 9(3):1165-1172, 1989.
Hui and Hashimoto, *Infect. Immun.*, 66(11):5329-5336, 1998.
Hussussian et al., *Nat. Genet.*, 8(1):15-21, 1994.
Ignatoski et al., *Br. J. Cancer*, 82(3):666-674, 2000.
Iijima and Devreotes, *Cell*, 109(5):599-610, 2002.
Innis et al., *PCR Protocols*, Academic Press, Inc., San Diego Calif., 1990.
Irie and Morton, *Proc. Natl. Acad. Sci. USA*, 83(22):8694-8698, 1986.
Irie et al., *Lancet.*, 1(8641):786-787, 1989.
Jacobs et al., *J. Clin. Oncol.*, 17(7):1974-1982, 1999.
Joki et al., *Cancer Res.*, 60(17):4926-31, 2000.
Ju et al., *J. Neuropathol. Exp. Neurol.*, 59(3):241-50, 2000.
Kamb et al., *Nat. Genet.*, 8(1):23-26, 1994a.
Kamb et al., *Science*, 2674:436-440, 1994b.
Kerr et al., *Br. J. Cancer*, 26(4):239-257, 1972.
Koul et al., *Oncogene*, 21:2357-2364, 2002.
Kwoh et al., *Proc. Natl. Acad. Sci. USA*, 86:1173, 1989.
Lee et al., *Nat. Biotechnol.*, 20(5):500-505, 2002.
Leslie and Downes, *Cell Signal*, 14(4):285-295, 2002.
Li and Sun, *Proc. Natl. Acad. Sci. USA*, 95:15406-15411, 1998.
Li et al., *Science* 28; 275:1943-1947, 1997.
Lu et al., *J. Biol. Chem.*, 278:40057-40066, 2003.
Lu et al., *Oncogene*, 18(50):7034-7045, 1999.
Marsters et al., *Recent Prog. Horm. Res.*, 54:225-234, 1999.
Mitchell et al., *Ann. NY Acad. Sci.*, 690:153-166, 1993.
Mitchell et al., *J. Clin. Oncol.*, 8(5):856-869, 1990.
Molina et al., *Cancer Res.*, 61(12):4744-4749, 2001.
Mori et al., *Cancer Res.*, 54(13):3396-3397, 1994.
Morton et al., *Arch. Surg.*, 127:392-399, 1992.
Moter et al., *J. Microbiol. Methods*, 41(2):85-112, 2000.
Muthuswamy and Muller, *Oncogene*, 11:1801-1810, 1995.
Mutter et al., *J. Natl. Cancer Inst.*, 92(11):924-930, 2000.
Nakamura et al., In: *Handbook of Experimental Immunology* (4$^{th}$ Ed.), Weir et al., (eds). 1:27, Blackwell Scientific Publ., Oxford, 1987.
Nath et al., *Biotech. Histochem.*, 73(1):6-22, 1998.
Nobri et al., *Nature (London)*, 368:753-756, 1995.
Ohara et al., *Proc. Natl. Acad. Sci. USA*, 86:5673-5677, 1989.
Okamoto et al., *Proc. Natl. Acad. Sci. USA*, 91(23):11045-11049, 1994.
Orlow et al., *Int. J. Oncol.*, 15(1):17-24, 1994.
Palka and Green, *J. Cell Sci.*, 110(19):2359-71, 1997.
Parsons and Simpson, *Methods Mol. Biol.*, 222:147-166, 2003.
PCT Appln. PCT/US87/00880
PCT Appln. PCT/US89/01025
PCT Appln. WO 88/10315
PCT Appln. WO 89/06700
PCT Appln. WO 90/07641
Pease et al., *Proc. Natl. Acad. Sci. USA*, 91:5022-5026, 1994.
Pegram et al., *J. Clin., Oncol.*, 16(8):2659-2671, 1998.
Perren et al., *Am. J. Pathol.*, 155(4):1253-1260, 1999.

Petit et al., *Am. J. Pathol.*, 151(6):1523-1530, 1997.
Pietras et al., *Oncogene,* 17(17):2235-2249, 1998.
Podsypanina et al., *Proc. Natl. Acad. Sci. USA,* 98:10320-10325, 2001.
Qin et al., *Proc. Natl. Acad. Sci. USA,* 95(24):14411-14416, 1998.
Ravindranath and Morton, *Intern. Rev. Immunol.,* 7:303-329, 1991.
Rosenberg et al., *Ann. Surg.* 210(4):474-548, 1989.
Rosenberg et al., *N. Engl. J. Med.,* 319:1676, 1988.
Sambrook et al., *In: Molecular cloning,* Cold Spring Harbor Laboratory Press, Cold Spring Harbor, NY, 2001.
Sano et al., *Science,* 258(5079):120-2, 1992.
Seidman et al., *J. Clin. Oncol.,* 19(10):2587-2595, 2001.
Serrano et al., *Nature,* 366:704-707, 1993.
Serrano et al., *Science,* 267(5195):249-252, 1995.
Shepard et al., *J. Clin. Immunol.,* 11:117-127, 1991.
Shoemaker et al., *Nature Genetics,* 14:450-456, 1996.
Slamon et al., *N. Engl. J. Med.,* 344(11):783-792, 2001.
Slamon et al., *Science,* 235(4785):177-182, 1987.
Slamon et al., *Science,* 244:707-712, 1989.
Sliwkowski et al., *Semin. Oncol.,* 26(4 Suppl 12):60-70, 1999.
Tan et al., *Mol. Cell,* 9:993-1004, 2002.
Teng et al., *Cancer Res.,* 57(23):5221-5225, 1997.
Tsujimoto and Croce, *Proc. Natl. Acad. Sci. USA,* 83(14):5214-5218, 1986.
Tsujimoto et al., *Science,* 228(4706):1440-1443, 1985.
Valero et al., *J. Clin. Oncol.,* 13:2886-2894., 1995.
Van Leeuwen et al., *Oncogene,* 5(4):497-503, 1990.
Vivanco and Sawyers, *Nat. Rev. Cancer,* 2(7):489-501, 2002.
Vogel et al., *J. Clin. Oncol.,* 20(3):719-726, 2002.
Walker et al., *Proc. Natl. Acad. Sci. USA,* 89:392-396 1992.
Weier et al., *Expert Rev. Mol. Diagn.,* 2(2):109-119, 2002.
Whang et al., *J. Natl. Cancer Inst.,* 90(11):859-861, 1998.
Wu et al., *Mol. Cell. Biochem.,* 203(1-2):59-71, 2000.
Xiong et al., *Cancer Res.,* 61(4):1727-1732, 2001.
Yakes et al., *Cancer Res.,* 62(14):4132-4141, 2002.
Yu and Hung, *Oncogene,* 19(53):6115-6121, 2000.
Yu et al., *Mol. Cell,* 2:581-591, 1998a.
Yu et al., *Oncogene,* 16:2087-2094, 199b.
Zhou et al., *J Biol Chem* 275, 8027-8031, 2000.

What is claimed is:

1. A method for administering a treatment regimen comprising an effective amount of a P13K inhibitor, said method comprising:
   (1) assaying a patient sample comprising at least one test cancer cell to measure the amount of PTEN protein having the amino acid sequence of SEQ ID NO:2 using at least one technique chosen from the group consisting of immunohistochemistry, immunoprecipitation, enzyme linked immunosorbent assay (ELISA), radioimmunoassay (RIA), immunoradiometric assay, fluoroimmunoassay, chemiluminescent assay, bioluminescent assay, western blot, antibody array, and FACS analysis;
   (2) comparing the amount of PTEN protein measured in (1) to a reference amount of PTEN protein in reference cancer cells of a reference cohort of patients who are not candidates for said treatment regimen; and
   (3) administering said treatment regimen to a test patient for whom said at least one test cancer cell is measured in (1) to have an absence of detectable PTEN protein or an amount of PTEN protein that is no more than 50% of said reference amount of PTEN protein in (2).

2. The method of claim 1, wherein said at least one test cancer cell is selected from the group consisting of breast cancer cells, lung cancer cells, ovarian cancer cells, brain cancer cells, gastrointestinal tract cancer cells, salivary duct cancer cells, endometrial cancer cells, prostate cancer cells, head & neck cancer cells, glioma cells, pancreatic cancer cells, hepatocellular cancer cells, myeloma cells, soft tissue sarcoma cells, and non-small cell lung cancer cells.

3. The method of claim 1, wherein said treatment regimen is administered to a test patient for whom said at least one test cancer cell is measured in (1) to have an absence of detectable PTEN protein or an amount of PTEN protein that is no more than 80% of said reference amount of PTEN protein in (2).

4. A method for administering a first treatment regimen comprising an effective amount of a PI3K inhibitor, said method comprising:
   (1) assaying a patient sample comprising at least one test cancer cell to measure the amount of PTEN protein having the amino acid sequence of SEQ ID NO:2 using at least one technique chosen from the group consisting of immunohistochemistry, immunoprecipitation, enzyme linked immunosorbent assay (ELISA), radioimmunoassay (RIA), immunoradiometric assay, fluoroimmunoassay, chemiluminescent assay, bioluminescent assay, western blot, antibody array, and FACS analysis;
   (2) comparing the amount of PTEN protein measured in (1) to a reference amount of PTEN protein in reference cancer cells of a reference cohort of patients who are not candidates for said first treatment regimen; and
   (3) (a) administering said first treatment regimen to a test patient for whom said at least one test cancer cell is measured in (1) to have an absence of detectable PTEN protein or an amount of PTEN protein that is no more than 50% of said reference amount of PTEN protein in (2); or
   (3) (b) administering a second treatment regimen comprising trastuzumab to a test patient for whom said at least one test cancer cell is measured in (1) to have an amount of PTEN protein that is greater than 50% of said reference amount of PTEN protein in (2).

5. The method of claim 4, wherein said at least one test cancer cell is selected from the group consisting of breast cancer cells, lung cancer cells, ovarian cancer cells, brain cancer cells, gastrointestinal tract cancer cells, salivary duct cancer cells, endometrial cancer cells, prostate cancer cells, head & neck cancer cells, glioma cells, pancreatic cancer cells, hepatocellular cancer cells, myeloma cells, soft tissue sarcoma cells, and non-small cell lung cancer cells.

6. The method of claim 4, wherein in (3)(a) said first treatment regimen is administered to a test patient for whom said at least one test cancer cell is measured in (1) to have an absence of detectable PTEN protein or an amount of PTEN protein that is no more than 80% of said reference amount of PTEN protein in (2); and in (3)(b) said second treatment regimen is administered to a test patient for whom said at least one test cancer cell is measured in (1) to have an amount of PTEN protein that is greater than 80% of said reference amount of PTEN protein in (2).

* * * * *

SEQUENCE LISTING

```
<160> NUMBER OF SEQ ID NOS: 4

<210> SEQ ID NO 1
<211> LENGTH: 1212
<212> TYPE: DNA
<213> ORGANISM: Homo sapiens
<220> FEATURE:
<221> NAME/KEY: CDS
<222> LOCATION: (1)..(1212)

<400> SEQUENCE: 1 atg aca gcc atc atc aaa gag atc gtt agc aga aac aaa agg aga tat      48
Met Thr Ala Ile Ile Lys Glu Ile Val Ser Arg Asn Lys Arg Arg Tyr
1               5                   10                  15 caa gag gat gga ttc gac tta gac ttg acc tat att tat cca aac att      96
Gln Glu Asp Gly Phe Asp Leu Asp Leu Thr Tyr Ile Tyr Pro Asn Ile
            20                  25                  30 att gct atg gga ttt cct gca gaa aga ctt gaa ggc gta tac agg aac     144
Ile Ala Met Gly Phe Pro Ala Glu Arg Leu Glu Gly Val Tyr Arg Asn
        35                  40                  45 aat att gat gat gta gta agg ttt ttg gat tca aag cat aaa aac cat     192
Asn Ile Asp Asp Val Val Arg Phe Leu Asp Ser Lys His Lys Asn His
    50                  55                  60 tac aag ata tac aat ctt tgt gct gaa aga cat tat gac acc gcc aaa     240
Tyr Lys Ile Tyr Asn Leu Cys Ala Glu Arg His Tyr Asp Thr Ala Lys
65                  70                  75                  80 ttt aat tgc aga gtt gca caa tat cct ttt gaa gac cat aac cca cca     288
Phe Asn Cys Arg Val Ala Gln Tyr Pro Phe Glu Asp His Asn Pro Pro
                85                  90                  95 cag cta gaa ctt atc aaa ccc ttt tgt gaa gat ctt gac caa tgg cta     336
Gln Leu Glu Leu Ile Lys Pro Phe Cys Glu Asp Leu Asp Gln Trp Leu
            100                 105                 110 agt gaa gat gac aat cat gtt gca gca att cac tgt aaa gct gga aag     384
Ser Glu Asp Asp Asn His Val Ala Ala Ile His Cys Lys Ala Gly Lys
        115                 120                 125 gga cga act ggt gta atg ata tgt gca tat tta tta cat cgg ggc aaa     432
Gly Arg Thr Gly Val Met Ile Cys Ala Tyr Leu Leu His Arg Gly Lys
    130                 135                 140 ttt tta aag gca caa gag gcc cta gat ttc tat ggg gaa gta agg acc     480
Phe Leu Lys Ala Gln Glu Ala Leu Asp Phe Tyr Gly Glu Val Arg Thr
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 145 |     |     |     |     | 150 |     |     |     |     | 155 |     |     | 160 |      |
| aga | gac | aaa | aag | gga | gta | act | att | ccc | agt | cag | agg | cgc | tat | gtg | tat | 528  |
| Arg | Asp | Lys | Lys | Gly | Val | Thr | Ile | Pro | Ser | Gln | Arg | Arg | Tyr | Val | Tyr |      |
|     |     |     |     | 165 |     |     |     |     | 170 |     |     |     |     | 175 |     |      |
| tat | tat | agc | tac | ctg | tta | aag | aat | cat | ctg | gat | tat | aga | cca | gtg | gca | 576  |
| Tyr | Tyr | Ser | Tyr | Leu | Leu | Lys | Asn | His | Leu | Asp | Tyr | Arg | Pro | Val | Ala |      |
|     |     |     | 180 |     |     |     |     | 185 |     |     |     |     | 190 |     |     |      |
| ctg | ttg | ttt | cac | aag | atg | atg | ttt | gaa | act | att | cca | atg | ttc | agt | ggc | 624  |
| Leu | Leu | Phe | His | Lys | Met | Met | Phe | Glu | Thr | Ile | Pro | Met | Phe | Ser | Gly |      |
|     |     | 195 |     |     |     |     | 200 |     |     |     |     | 205 |     |     |     |      |
| gga | act | tgc | aat | cct | cag | ttt | gtg | gtc | tgc | cag | cta | aag | gtg | aag | ata | 672  |
| Gly | Thr | Cys | Asn | Pro | Gln | Phe | Val | Val | Cys | Gln | Leu | Lys | Val | Lys | Ile |      |
|     | 210 |     |     |     |     | 215 |     |     |     |     | 220 |     |     |     |     |      |
| tat | tcc | tcc | aat | tca | gga | ccc | aca | cga | cgg | gaa | gac | aag | ttc | atg | tac | 720  |
| Tyr | Ser | Ser | Asn | Ser | Gly | Pro | Thr | Arg | Arg | Glu | Asp | Lys | Phe | Met | Tyr |      |
| 225 |     |     |     |     | 230 |     |     |     |     | 235 |     |     |     |     | 240 |      |
| ttt | gag | ttc | cct | cag | ccg | tta | cct | gtg | tgt | ggt | gat | atc | aaa | gta | gag | 768  |
| Phe | Glu | Phe | Pro | Gln | Pro | Leu | Pro | Val | Cys | Gly | Asp | Ile | Lys | Val | Glu |      |
|     |     |     |     | 245 |     |     |     |     | 250 |     |     |     |     | 255 |     |      |
| ttc | ttc | cac | aaa | cag | aac | aag | atg | cta | aaa | aag | gac | aaa | atg | ttt | cac | 816  |
| Phe | Phe | His | Lys | Gln | Asn | Lys | Met | Leu | Lys | Lys | Asp | Lys | Met | Phe | His |      |
|     |     |     | 260 |     |     |     |     | 265 |     |     |     |     | 270 |     |     |      |
| ttt | tgg | gta | aat | aca | ttc | ttc | ata | cca | gga | cca | gag | gaa | acc | tca | gaa | 864  |
| Phe | Trp | Val | Asn | Thr | Phe | Phe | Ile | Pro | Gly | Pro | Glu | Glu | Thr | Ser | Glu |      |
|     |     | 275 |     |     |     |     | 280 |     |     |     |     | 285 |     |     |     |      |
| aaa | gta | gaa | aat | gga | agt | cta | tgt | gat | caa | gaa | atc | gat | agc | att | tgc | 912  |
| Lys | Val | Glu | Asn | Gly | Ser | Leu | Cys | Asp | Gln | Glu | Ile | Asp | Ser | Ile | Cys |      |
|     | 290 |     |     |     |     | 295 |     |     |     |     | 300 |     |     |     |     |      |
| agt | ata | gag | cgt | gca | gat | aat | gac | aag | gaa | tat | cta | gta | ctt | act | tta | 960  |
| Ser | Ile | Glu | Arg | Ala | Asp | Asn | Asp | Lys | Glu | Tyr | Leu | Val | Leu | Thr | Leu |      |
| 305 |     |     |     | 310 |     |     |     |     | 315 |     |     |     |     |     | 320 |      |
| aca | aaa | aat | gat | ctt | gac | aaa | gca | aat | aaa | gac | aaa | gcc | aac | cga | tac | 1008 |
| Thr | Lys | Asn | Asp | Leu | Asp | Lys | Ala | Asn | Lys | Asp | Lys | Ala | Asn | Arg | Tyr |      |
|     |     |     |     | 325 |     |     |     |     | 330 |     |     |     |     | 335 |     |      |
| ttt | tct | cca | aat | ttt | aag | gtg | aag | ctg | tac | ttc | aca | aaa | aca | gta | gag | 1056 |
| Phe | Ser | Pro | Asn | Phe | Lys | Val | Lys | Leu | Tyr | Phe | Thr | Lys | Thr | Val | Glu |      |
|     |     |     | 340 |     |     |     |     | 345 |     |     |     |     | 350 |     |     |      |
| gag | ccg | tca | aat | cca | gag | gct | agc | agt | tca | act | tct | gta | aca | cca | gat | 1104 |
| Glu | Pro | Ser | Asn | Pro | Glu | Ala | Ser | Ser | Ser | Thr | Ser | Val | Thr | Pro | Asp |      |
|     |     | 355 |     |     |     |     | 360 |     |     |     |     | 365 |     |     |     |      |
| gtt | agt | gac | aat | gaa | cct | gat | cat | tat | aga | tat | tct | gac | acc | act | gac | 1152 |
| Val | Ser | Asp | Asn | Glu | Pro | Asp | His | Tyr | Arg | Tyr | Ser | Asp | Thr | Thr | Asp |      |
|     | 370 |     |     |     |     | 375 |     |     |     |     | 380 |     |     |     |     |      |
| tct | gat | cca | gag | aat | gaa | cct | ttt | gat | gaa | gat | cag | cat | aca | caa | att | 1200 |
| Ser | Asp | Pro | Glu | Asn | Glu | Pro | Phe | Asp | Glu | Asp | Gln | His | Thr | Gln | Ile |      |
| 385 |     |     |     |     | 390 |     |     |     |     | 395 |     |     |     |     | 400 |      |
| aca | aaa | gtc | tga |     |     |     |     |     |     |     |     |     |     |     |     | 1212 |
| Thr | Lys | Val |     |     |     |     |     |     |     |     |     |     |     |     |     |      |

<210> SEQ ID NO 2
<211> LENGTH: 403
<212> TYPE: PRT
<213> ORGANISM: Homo sapiens

<400> SEQUENCE: 2

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

```
Ile Ala Met Gly Phe Pro Ala Glu Arg Leu Glu Val Tyr Arg Asn
         35                  40                  45

Asn Ile Asp Asp Val Val Arg Phe Leu Asp Ser Lys His Lys Asn His
 50                  55                  60

Tyr Lys Ile Tyr Asn Leu Cys Ala Glu Arg His Tyr Asp Thr Ala Lys
 65                  70                  75                  80

Phe Asn Cys Arg Val Ala Gln Tyr Pro Phe Glu Asp His Asn Pro Pro
                 85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
            115                 120                 125

Gly Arg Thr Gly Val Met Ile Cys Ala Tyr Leu Leu His Arg Gly Lys
130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
            195                 200                 205

Gly Thr Cys Asn Pro Gln Phe Val Val Cys Gln Leu Lys Val Lys Ile
            210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Glu Ile Asp Ser Ile Cys
290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Ser Thr Ser Val Thr Pro Asp
            355                 360                 365

Val Ser Asp Asn Glu Pro Asp His Tyr Arg Tyr Ser Asp Thr Thr Asp
370                 375                 380

Ser Asp Pro Glu Asn Glu Pro Phe Asp Glu Asp Gln His Thr Gln Ile
385                 390                 395                 400

Thr Lys Val

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 3
ctgctagcct ctggatttga                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
cttctggcat ccggtttaga                                              20
```